United States Patent
Kovarik et al.

(10) Patent No.: US 8,833,817 B2
(45) Date of Patent: *Sep. 16, 2014

(54) SELECTIVELY BENDABLE ANIMAL WASTE SCOOPER FOR SANITARY HANDLING OF ANIMAL DROPPINGS

(71) Applicants: Carter J. Kovarik, Englewood, CO (US); Joseph E. Kovarik, Englewood, CO (US)

(72) Inventors: Carter J. Kovarik, Englewood, CO (US); Joseph E. Kovarik, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/163,521

(22) Filed: Jan. 24, 2014

(65) Prior Publication Data

US 2014/0137811 A1    May 22, 2014

Related U.S. Application Data

(63) Continuation-in-part of application No. 14/078,830, filed on Nov. 13, 2013, which is a continuation-in-part of application No. 13/771,813, filed on Feb. 20, 2013, now Pat. No. 8,585,114, application No. 14/163,521, which is a continuation-in-part of application No. 29/462,798, filed on Aug. 8, 2013.

(60) Provisional application No. 61/601,789, filed on Feb. 22, 2012.

(51) Int. Cl.
*A01K 29/00* (2006.01)
*E01H 1/12* (2006.01)
*B25J 1/02* (2006.01)
*A01K 27/00* (2006.01)

(52) U.S. Cl.
CPC ............ *E01H 1/1206* (2013.01); *A01K 27/004* (2013.01); *E01H 2001/1273* (2013.01); *B25J 1/02* (2013.01)
USPC ............ 294/1.4; 294/19.2; 294/111; 294/210

(58) Field of Classification Search
CPC .................... E01H 1/1206; E01H 2001/1273; B25J 1/02
USPC .......... 294/1.4, 1.5, 19.2, 111, 115, 190, 209, 294/210; 81/177.6; 606/205
See application file for complete search history.

(56) References Cited

U.S. PATENT DOCUMENTS 388,776 A    8/1888 Hall
826,160 A    7/1906 Hall
(Continued)

FOREIGN PATENT DOCUMENTS

FR    1080718    12/1954

OTHER PUBLICATIONS

"Robot Claw Grabber" by Toysmith, Feb. 27, 2005, [retrieved on Aug. 16, 2013], 3 pages. Retrieved from: http://web.archive.org/web/20050227054600/http://www.toys2wish4.com/robclawgrab.html.

(Continued)

*Primary Examiner* — Dean Kramer
(74) *Attorney, Agent, or Firm* — Sheridan Ross P.C.

(57) ABSTRACT

An animal waste scooper has a flexible extension adapted to be reversibly coiled such that when it is uncoiled, a trigger operated jaws/scooping portion of the device is employed to pick up waste. The flexible scooper device includes a handle with a trigger, a flexible, preferably corrugated extension assembly and a pair of jaws. Other embodiments are directed to a reversibly flexible, bendable hand operated device for grasping a golf ball from the ground from a standing position.

20 Claims, 15 Drawing Sheets

(56) References Cited

U.S. PATENT DOCUMENTS

| | | |
|---|---|---|
| 944,214 A | 12/1909 | Rydquist |
| 1,051,374 A | 1/1913 | Agin |
| 1,519,938 A | 12/1924 | Smith |
| 2,613,100 A | 10/1952 | Casey |
| 2,616,741 A | 11/1952 | Ziese |
| 2,947,564 A | 8/1960 | Winther |
| 3,219,376 A | 11/1965 | Peters |
| 3,266,059 A | 8/1966 | Stelle |
| 3,328,066 A | 6/1967 | Johnston |
| 3,346,293 A | 10/1967 | Wilcox |
| 3,527,492 A | 9/1970 | Hollis |
| 3,576,343 A | 4/1971 | Juhlin et al. |
| 3,617,084 A | 11/1971 | Mares |
| 3,761,121 A | 9/1973 | Reid |
| 3,901,545 A | 8/1975 | Shott |
| 3,912,316 A | 10/1975 | Veech |
| 3,934,915 A | 1/1976 | Humpa |
| 4,033,618 A | 7/1977 | Lamb |
| 4,039,216 A | 8/1977 | Soos |
| 4,179,145 A | 12/1979 | Shinsako |
| 4,186,955 A | 2/1980 | Campbell |
| 4,225,174 A | 9/1980 | Hennessy et al. |
| 4,248,468 A | 2/1981 | Hastings |
| 4,253,697 A | 3/1981 | Acosta |
| 4,272,116 A | 6/1981 | Tufte, Jr. |
| 4,374,600 A | 2/1983 | van Zelm |
| 4,393,728 A | 7/1983 | Larson et al. |
| 4,398,759 A | 8/1983 | Manola |
| 4,483,562 A | 11/1984 | Schoolman |
| 4,501,230 A | 2/1985 | Talo |
| 4,613,179 A | 9/1986 | van Zelm |
| 4,647,094 A | 3/1987 | Bergkvist et al. |
| 4,669,769 A | 6/1987 | Polder, Jr. |
| 4,709,839 A | 12/1987 | Tucker |
| 4,758,035 A | 7/1988 | Shimasaki |
| 4,863,204 A | 9/1989 | Peters |
| 4,865,371 A | 9/1989 | Egberg |
| 4,878,703 A | 11/1989 | Yoshioka |
| 4,962,957 A | 10/1990 | Traber |
| 5,154,465 A | 10/1992 | Pakosh |
| 5,380,054 A | 1/1995 | Galvis |
| 5,503,442 A | 4/1996 | Lee |
| 5,540,470 A | 7/1996 | Lu |
| 5,572,913 A | 11/1996 | Nasiell |
| 5,577,785 A | 11/1996 | Traber et al. |
| 5,590,923 A | 1/1997 | Berger et al. |
| 5,601,321 A | 2/1997 | Simon |
| 5,628,537 A | 5/1997 | Kiemer |
| 5,647,622 A | 7/1997 | Schectman |
| 5,667,146 A | 9/1997 | Pimentel et al. |
| 5,707,303 A | 1/1998 | Berkowitz et al. |
| 5,766,196 A | 6/1998 | Griffiths |
| 5,778,939 A | 7/1998 | Hok-Yin |
| 5,822,908 A | 10/1998 | Blanchard |
| 5,823,592 A | 10/1998 | Kalidindi |
| 5,857,723 A | 1/1999 | Mathieu et al. |
| 5,895,082 A | 4/1999 | Kaluzny |
| 6,042,155 A | 3/2000 | Lockwood |
| 6,062,618 A | 5/2000 | Figueroa |
| 6,148,773 A | 11/2000 | Bogdahn |
| D439,402 S | 3/2001 | Johnson |
| 6,257,634 B1 | 7/2001 | Wei |
| 6,457,761 B1 | 10/2002 | Benoit |
| 6,508,496 B1 | 1/2003 | Huang |
| 6,513,844 B1 | 2/2003 | Hsu |
| 6,520,556 B1 | 2/2003 | Hsu |
| 6,571,479 B1 | 6/2003 | Wu |
| 6,648,261 B2 | 11/2003 | Irving |
| 6,669,254 B2 | 12/2003 | Thom et al. |
| 6,739,637 B2 | 5/2004 | Hsu |
| 6,796,587 B2 | 9/2004 | Tsou |
| 6,845,736 B1 | 1/2005 | Anderson |
| 6,848,731 B2 | 2/2005 | Khubani et al. |
| 6,874,833 B2 | 4/2005 | Keith et al. |
| 6,971,695 B2 | 12/2005 | Backstrom |
| 7,004,520 B2 | 2/2006 | Khubani et al. |
| 7,093,869 B2 | 8/2006 | Jung |
| 7,325,849 B2 | 2/2008 | Jones |
| 7,338,434 B1 | 3/2008 | Haarstad et al. |
| 7,344,171 B1 | 3/2008 | McMullan |
| 7,448,659 B1 | 11/2008 | Auseklis |
| D591,122 S | 4/2009 | Buzby et al. |
| 7,533,906 B2 | 5/2009 | Luettgen et al. |
| 7,665,782 B2 | 2/2010 | Buzby et al. |
| 7,677,619 B2 | 3/2010 | Hutchings et al. |
| 7,695,035 B2 | 4/2010 | Sumner et al. |
| 7,744,136 B2 | 6/2010 | Waltz |
| 7,854,738 B2 | 12/2010 | Lee et al. |
| D632,069 S | 2/2011 | Thiessens |
| 7,934,756 B2 | 5/2011 | Kroeze |
| 7,980,609 B2 | 7/2011 | Khubani |
| 7,992,907 B1 | 8/2011 | DeJesus |
| 8,061,751 B2 | 11/2011 | Hatcher |
| 8,091,936 B1 | 1/2012 | Graziano |
| 8,449,007 B2 | 5/2013 | Farmer |
| 8,528,850 B2 | 9/2013 | Bogdahn |
| 8,529,379 B2 | 9/2013 | Faircloth |
| 8,585,114 B2 | 11/2013 | Kovarik et al. |
| 8,602,917 B2 | 12/2013 | Bennett |
| 2003/0236549 A1 | 12/2003 | Bonadio et al. |
| 2004/0236316 A1 | 11/2004 | Danitz et al. |
| 2005/0057055 A1 | 3/2005 | Deal |
| 2006/0206101 A1* | 9/2006 | Lee .................. 606/1 |
| 2010/0021279 A1 | 1/2010 | Buzby et al. |
| 2010/0096866 A1* | 4/2010 | Flinn |
| 2012/0060878 A1 | 3/2012 | Thiessens |
| 2014/0047757 A1 | 2/2014 | Miller et al. |
| 2014/0054912 A1 | 2/2014 | Bustos |

OTHER PUBLICATIONS

International Search Report and Written Opinion for International (PCT) Patent Application No. PCT/US2013/054275 mailed Jan. 10, 2014, 10 pages.
Official Action for U.S. Appl. No. 13/771,813 mailed Jun. 14, 2013, 9 pages.
Official Action for U.S. Appl. No. 13/771,813 mailed Sep. 5, 2013, 9 pages.
Notice of Allowance for U.S. Appl. No. 13/771,813 mailed Sep. 20, 2013, 6 pages.
U.S. Appl. No. 29/462,798, filed Aug. 8, 2013, Kovarik et al.
U.S. Appl. No. 14/078,830, filed Nov. 13, 2013, Kovarik et al.
Official Action for U.S. Appl. No. 14/078,830 mailed Mar. 17, 2014, 7 pages.
Notice of Allowance for U.S. Appl. No. 14/078,830 mailed Apr. 11, 2014, 5 pages.
U.S. Appl. No. 14/290,207, filed May 29, 2014 Kovarik et al.

* cited by examiner

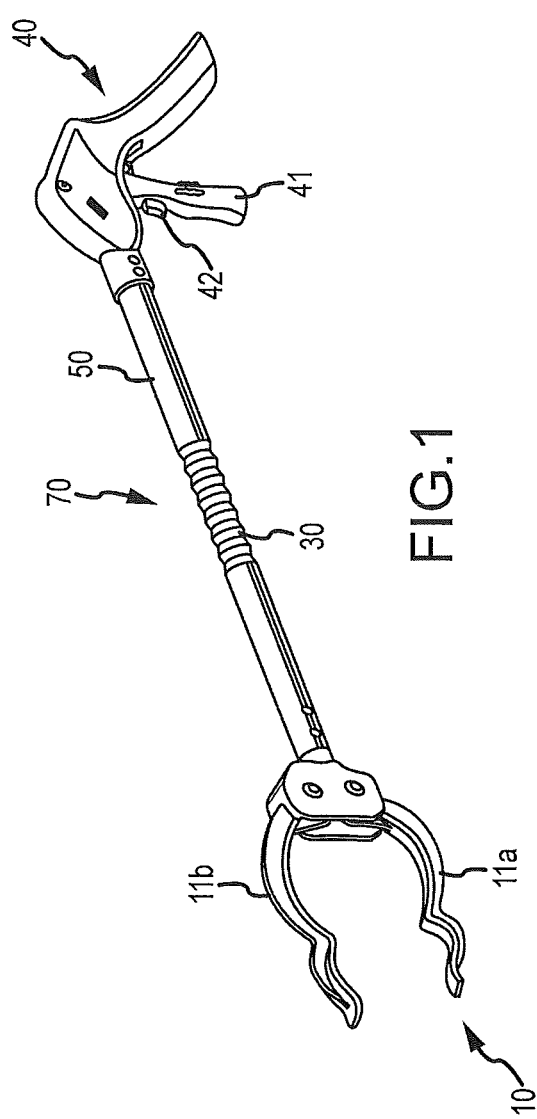
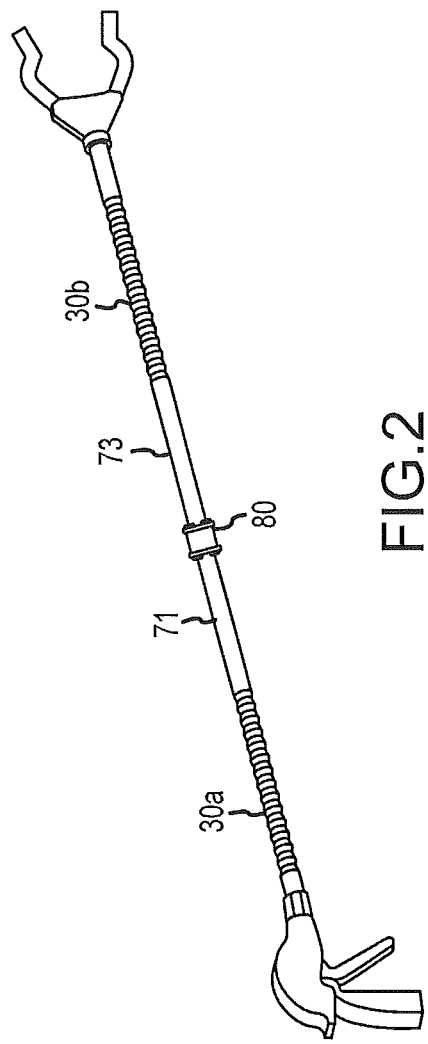
FIG.1
FIG.2

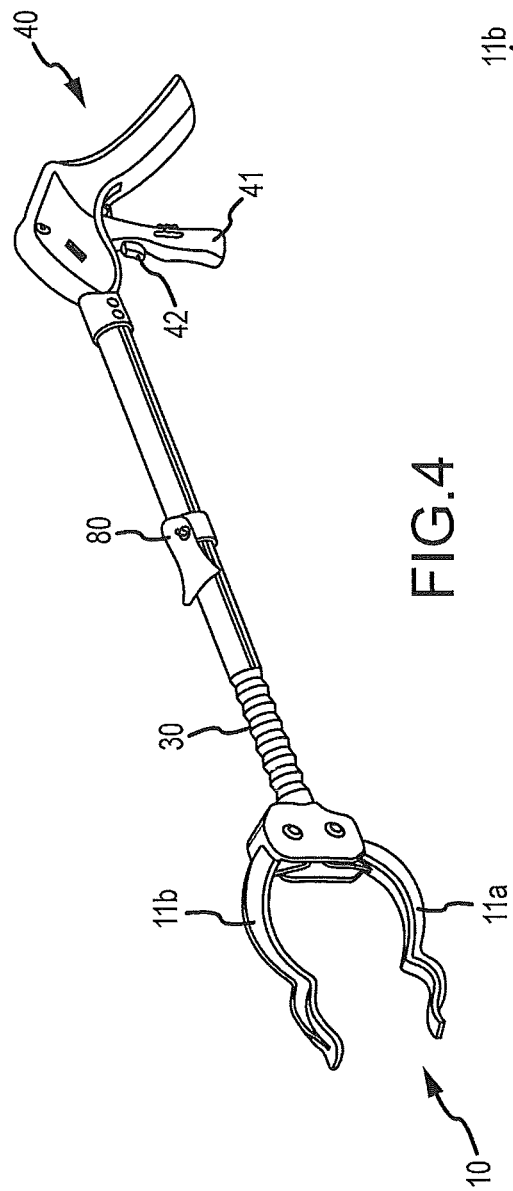
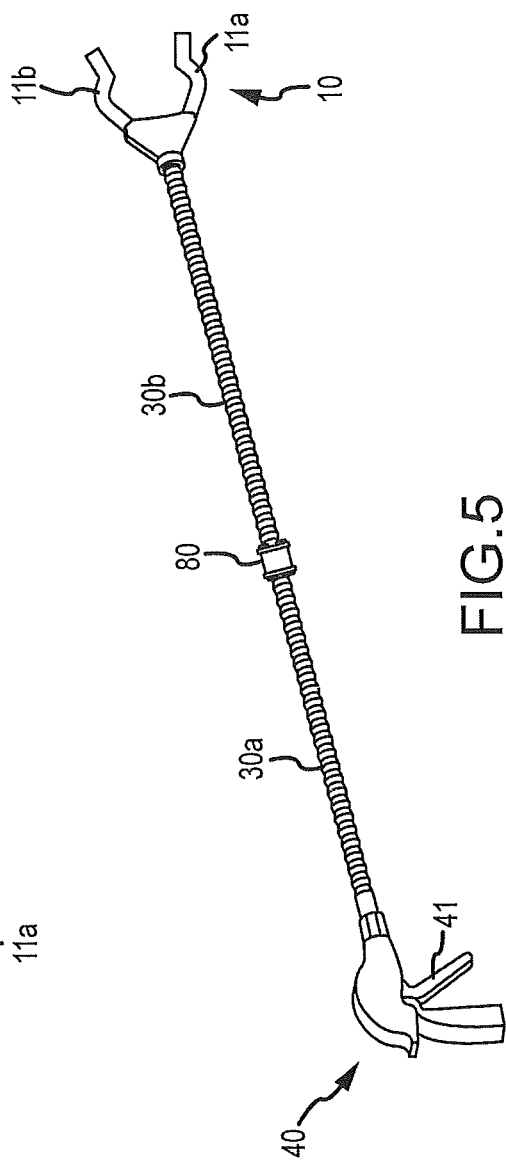

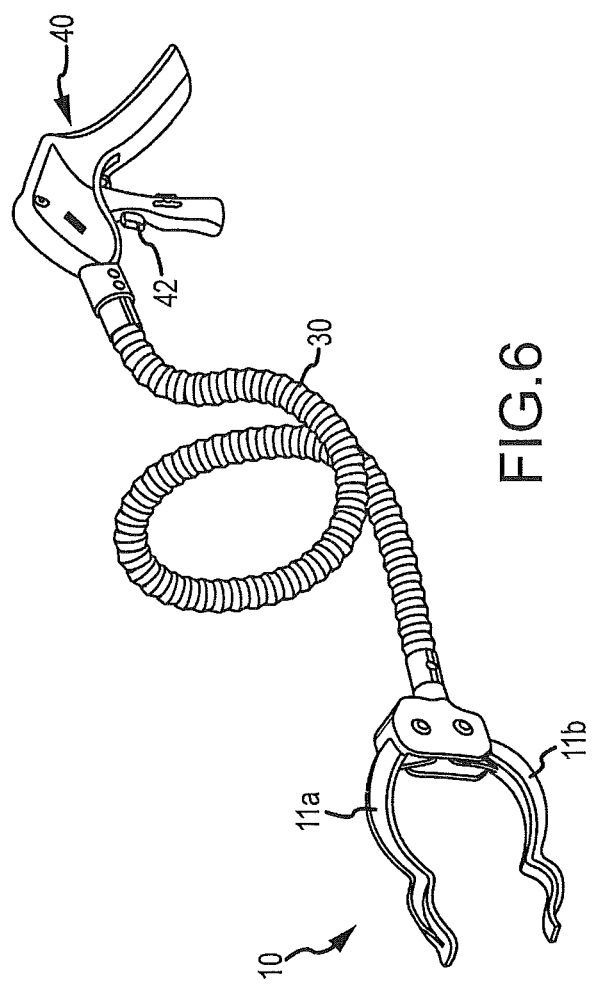

SELECTIVELY BENDABLE ANIMAL WASTE SCOOPER FOR SANITARY HANDLING OF ANIMAL DROPPINGS

RELATED APPLICATIONS

This application is a continuation-in-part application of U.S. patent application Ser. No. 14/078,830 filed on Nov. 13, 2013, which is a continuation-in-part of U.S. patent application Ser. No. 13/771,813 filed on Feb. 20, 2013, now issued U.S. Pat. No. 8,585,114, and claims priority from U.S. Provisional Patent Application Ser. No. 61/601,789, filed on Feb. 22, 2012. This application also seeks priority from U.S. patent application Ser. No. 29/462,798, filed Aug. 8, 2013. The entire disclosure of the prior applications are considered to be part of the disclosure of the accompanying application and are hereby incorporated by reference.

FIELD OF THE INVENTION

The present invention relates generally to hand-operated, grasping devices and more particularly to an animal waste scooper that has a flexible, preferably corrugated extension, with a trigger at one end and a jaw-like scooper on the other end, for sanitary handling of animal droppings from pet dogs, cats, and the like, of the type commonly referred to as a pooper scooper. Other embodiments are directed to placing and retrieving golf balls with a similar device.

BACKGROUND OF THE INVENTION

When being walked, pets frequently have the need to answer nature's call. In many instances, this requires the pet owner to "clean up" after their pet. Such activity typically occurs by the pet owner bending down and using their hands to scoop the pet waste into a plastic bag. Such a method may present difficulty for pet owners who are not flexible or able to bend in such a position. Further, some pet owners may not want to risk potential contact with the pet waste and may opt not to clean up after their pet.

Pet waste left in public areas such as streets and sidewalks creates numerous sanitary problems, particularly in metropolitan areas having high population densities. It has been estimated that there are currently 60 million dogs in the United States alone, many of which residing in large urban areas. Many municipalities have enacted local ordinances requiring that the pet owner clean up after their pets. Many dog owners resort to the "bag-in-hand" method to pick up their pet's waste. Many pet owners carry one or more plastic bags with them to collect such refuse. This entails a rather unpleasant operation that includes putting the bag on one's hand and grabbing the fecal material from the ground, carefully wrapping the fecal contents in the bag without touching the skin of the pet owner, and then having to tie the bag and either carry it in a pocket, on the leash or in a free hand until it can be disposed of.

Some longtime dog owners have resigned to this primitive method, but new owners are understandably repulsed by the above-described technique. It is therefore clear that a need exists for devices that provide clean and efficient collection and disposal of pet waste, in a convenient and sanitary fashion.

Many types of pet waste collecting devices have been devised for clean-up purposes. Some, for example, may be operated with one hand and without necessitating bending over or stooping. Such devices, sometimes called "pooper scoopers"—include those having cooperating jaws at the lower end of a relatively long, rigid cane-like handle, and some even make provision for collecting the refuse material in an open refuse bag, the refuse material entering the open end of the bag.

When pet owners take their pets for a walk, the pet owner often has at least a leash to restrain their pet and often employs a retractable leash to provide their pet with the ability to move ahead of them at different distances, while the owner retains control over such lengths via the retractable leash. Having to carry yet another tool, such as a conventional so-called "pooper scooper" device, is cumbersome and adds considerable hassle and complexity to the simple task of walking a pet. There is a long felt but unsolved need to provide a pet owner with a single tool that both provides the advantages of a retractable leash and a waste pick-up tool, such that a single device can facilitate more enjoyable pet/owner experience while on walks.

Moreover, in the area of ground and yard maintenance, whether public or private, it is often the case that garbage and debris is left on the ground or blown in by winds. For those individuals with pets or in rural areas, there is often the deposition of fecal matter by pets or wild animals roaming the grounds. As such, in order to maintain a clean and healthy environment for people, someone must periodically pick up, bag and dispose of the garbage, debris, fecal matter and other miscellaneous matter deposited on the ground. In public and business areas, this is typically accomplished by a maintenance crew, whereas in private locations it is done by the property dweller. To do this task in a sanitary and convenient way, a collection and bagging device that allows a user's hands to be distant and/or separated from the refuse and/or feces when collecting, bagging and disposing of the refuse is desirable.

In the general field of having to bend over and hand-manipulate an item, it will be appreciated that playing golf requires that a golfer repeatedly bend over to place or pick up the ball. The teeing, placement and collection of balls from the ground can be challenging for disabled or elderly players. Thus there is a need for a simple device that can be carried and transported by a golfer to make playing the game of golf easier, especially for older golfers and those with bad backs or who have limited flexibility.

SUMMARY OF THE INVENTION

The present invention relates to collection devices, and more specifically, to collapsible devices for collecting and bagging trash, garbage, debris and animal feces left on the ground without requiring the user to bend over or to manually touch the collected items. In various embodiments, the present invention is directed to a selectively bendable, hand-operated animal waste scooper that has a flexible, preferably corrugated extension, with a trigger at one end and a jaw-like scooper on the other end (e.g. having opposing claw halves), for sanitary handling of animal droppings from pets. In various embodiments, the animal scooper, waste gripping tool includes a jaw portion having a pair of jaws movable relative to each other between fully clamped and fully opened positions thereof, a handle portion spaced apart from the jaw portion by a bendable central portion that has a hollow, corrugated member having alternating ridges and grooves that is bendable so as to attain a predetermined shape.

In certain preferred embodiments, the central column of the device comprises a corrugated segment comprising a plurality of interconnected connectors, such as "loc-line" plastic elements. For certain embodiments that include the use of particular linked plastic components that comprise the flexible portion of the scooper device, incorporated entirely by this reference are U.S. Pat. No. 6,042,155 to Lockwood; U.S. Pat. No. 5,778,939 to Hok-Yin; U.S. Pat. No. 5,667,146 to Pimental et al.; and U.S. Pat. No. 7,533,906 to Luettgen.

In other embodiments, the hand-held waste scooper device includes a scooping portion having a scooper element movable relative to between a fully clamped position and a fully opened position. A handle portion is spaced apart from the scooping portion by a central portion, with the central portion comprising at least two separate portions comprising a hollow, corrugated member having alternating ridges and grooves. The corrugated member is bendable so as to attain a predetermined shape so that a user can preposition the central portion into a desired bent configuration. The handle portion comprises a first manually-actuatable trigger operatively connected to the scooping portion by a pull member at least substantially disposed within the central portion. Actuation of the trigger is operative to move the pull member to thereby selectively position the scooping elements between the fully clamped position and the fully opened position. The pull member preferably comprises at least one cord operatively connecting the handle portion to the scooping portion, with the at least one cord extending through said central portion. In certain embodiments, at least two separate portions of the central portion preferably comprise a plurality of interconnected connectors which together define a passageway through which said pull member passes through. In preferred embodiments, the plurality of interconnected connectors are in engagement with each other such that the interconnected connectors permit pivoting movement between the interconnected connectors.

While preferred embodiments of the present invention are directed to either a flexible fecal waste retrieval tool that can be coiled so that a pet owner can more easily carry such tool with them on pet walks, other embodiments include the inventive concept of combining a retractable leash device with a waste retrieval device. There is a current need for a pet waste collection tool having an integrated leash that is lightweight, compact, and easy to use. One of skill in the art, with the guidance provided herein, will appreciate the myriad ways by which such a combination can be achieved, but one in particular involves the combination of a retractable leash device connected to an extendable "pooper scooper"-type device. Such extension includes not only the preferred employment of at least one flexible, corrugated column portion as described herein, but also includes other telescoping mechanisms that facilitate such extension, where such telescoping mechanisms are connected to a housing of a retractable leash device. In one embodiment where a compact dual-function retractable leash and waste scooper is desired, a loc-line extended member is connected at one end to a scooper element (e.g. a pair of opposing jaw/scoops adapted to encompass fecal material when clamped together) is connected directly to the housing of a reeled leash such that mere physical manipulation of the loc-line member (e.g. from a coiled configuration to an extended position (with the coiled extension being from at least about 3 inches, more preferably at least about 6 inches in length, even more preferably 20 inches or more in length, and most preferably about 30 inches). The flexible nature of the device permits the pet owner to pre-position the angle of the scooping jaws in relationship to the ground where pet waste may reside such that a cleaner pickup of the waste can be achieved without requiring the owner to touch the waste using their hand placed in a bag. The present invention is superior to prior art "pooper-scooper" devices because the extended rigid pole that attaches to the scooper end of the device do not permit angular adjustment of the scooping section. In contrast, using the present invention, by manually adjusting the flexible portion of the extended member of the present invention, a pet owner can decide how best to approach any given deposit of pet waste, for example, by choosing to position the jaws in a manner that one jaw scrapes along the lowermost portion of the ground contacting waste, while the other jaw resides above such waste, permitting the owner to then clamp down on the jaws (via operation of the handle mounted trigger) and thus encapsulate the waste within the jaws. In preferred embodiments, the jaws are adapted to receive a bag pre-positioned about the open jaws prior to the waste recovery operation, thus achieving the desired bagging of the waste without the owner having to perform the above mentioned bag-in-hand method of waste retrieval.

In still other embodiments the issue as to what to do with the bagged waste is addressed by having the housing of the retractable leash provided with a portion that receives and dispenses bags. A bag dispenser can be of various shapes and sizes but accomplishes the basic task of providing ready access to bags for use with the scooping element of many embodiments of the present invention. Preferably such a bag receptacle is a refillable compartment that holds a plurality, e.g. about 20 biodegradable, disposable bags, able to accommodate most store purchased bag refills of both side pull (standard) or bottom pull types. For example, in combination with the associated pet waste scooping mechanism operably associated with the housing of a retractable leash, other desired features include not only flashlights, but also an associated receptacle for pet waste bags.

In certain embodiments, the bags employed have a closing ability such that once the scoop jaw of the waste gripping tool encircles the waste, with a bag pre-positioned over the scoop/jaw prior to contacting the waste, the bag is closed via the pressure applied by the perimeter of the scoop/jaw when the user operates the trigger to not only close the scoop/jaws. Certain types of closure elements can be employed to accomplish this closure function, including but not limited to adhesive being applied to one or both opposing sides of an open bag in the area where the scoop/jaws contact each other in the closed positron. Other closure mechanisms involve the use of zip-lock mating features (e.g. zip-lock bags, etc.) such that the closed position of the jaws causes the zip-lock elements of the bag employed to seal the bag with the waste contents inside.

In certain embodiments, the interiors of opposing scoop/jaw surface are fitted with a disposable liner, such as a biodegradable bag, prior to use such that the bag forms a covering to surround and encapsulate pet waste. The bag protects the pet-debris scooper from soiling by pet waste during collection. The peripheral ends of the liner are attached to the outside of scoop/jaws with the peripheral edge of the disposable bag including an adhesive strip adapted to adhere the edge of disposable bag, and also may be provided to ensure a better contact and connection with one or both of the jaw/scoop features. The bag is thus positioned and retained on the scoop/jaws. As one of skill will appreciate, various other bag retention features, such as elastomeric bands, clips, etc. can be employed to secure the bag in a fashion such that it remains in contact with the jaws/scoop during the waste pick-up operation.

One aspect of the present invention is directed to effectively sealing the waste inside a bag after collection. While the above method employing adhesives is preferred, others can also be used, such as with ties, twisting of the bag, spinning the bag after it is filled with waste, etc. Thus various types of bag fasteners or closure techniques may include a wide variety of devices that clamp, seal, fasten, hold, squeeze, or otherwise close the ends of the individual portions of a bag filled with waste. Such fasteners may thus include ratchet ties, wire tie-type systems, such as a metal or wire twist tie, spring clamps, bands, adhesive tabs, peel seals, zippers, zip-locks, slider mechanisms, Velcro, or other devices to gather and hold the bag material in a tight or secure fashion.

The waste refuse collecting device as briefly described above is capable of use in picking up a wide variety of refuse, but many embodiments are designed primarily for picking up animal droppings or excrement such as may be left on a sidewalk or lawn, and when so used, it is designed to have associated therewith a disposable, excrement-collecting bag. Such device can, however, also be used to pick up a variety of other refuse without using a bag. Thus, in other embodiments, the refuse collecting device is usable for picking up a wide variety of litter without necessitating the use of the disposable bag. However, where dog or other animal excrement is concerned, or whether semi-solid garbage matter which has been spilled outdoors is to be collected, the use of the bag is highly desirable. Certain embodiments include either two movable jaws, or a fixed jaw and a pivotally mounted jaw, preferably of similar design and each being in a dished-shaped configuration.

When picking up a quantity of excrement or refuse, the flexible nature of the present invention permits a user to adjust the jaw portion to be at any desired angle to facilitate the use of one of the jaws as a scoop for sliding beneath the refuse. The refuse can then enter the reversed or inverted bottom portion of the bag and when it has thus been completely scooped or when at least a major portion of the refuse has been scooped, the operator can operate the trigger by exerting a squeezing action on the trigger, thereby causing the movable jaw to move to its closed position and the cuffed portion of the bag may be "peeled" downwardly and removed from the jaws, after which a conventional twist wire or other closure means (zip-lock bags, etc.) can be applied to the peeled portion of the bag. The bag and its contents may then be removed from between the jaws and disposed of in any suitable manner.

From the above description, it will be apparent that an extremely sanitary method of picking up refuse, particularly animal refuse, is provided, with numerous advantages that include no contact whatsoever of the hands of the user or operator with the refuse is resorted to. Furthermore, only one hand is required for the operation of the device. Still further, little or no stooping or bending of the user's body is necessary when using the device. Finally, after the excrement or refuse-filled bag is disposed of, the device remains substantially clean and does not require washing, rinsing, or the like. It may simply be put on the shelf or otherwise stored for future use by the application thereto of a fresh disposable bag. The present invention, due partially to its ability to assume a compact dimension, such as being coiled for easy transport and storage, can be carried by a pet owner in a purse, a suitcase, on airplanes, cars, buses, etc. without the problems associated with attempting to bring a conventional "pooper-scooper" rigid can-like device with them. Thus, both carrying of such a coiled device on pet walks, as well as travelling with such a device on transportation vehicles, makes the provision of such a device when desired far more practicable.

In preferred embodiments, the collecting, bagging and disposing device is achieved with a device that can be easily transported in a collapsible, bent, coiled or telescoping manner in order to have more efficient storage of the device when not in use or when transporting the device.

In certain embodiments, the device has curved jaws or clamshell scoops and an elongated handle for collecting trash and may employ a bag for the collected trash/waste material. In other embodiments, the jaws are designed such that they are able to get underneath the feces or trash in order to assure that the material being collected does not get smashed in the jaw teeth. The provision of at least one flexible portion along the member that attaches the handle region to the jaws at the opposite end, enables a user to pre-position the device for maximum effectiveness in picking up any given waste.

Preferably, embodiments of the present invention provide a one handed means for getting underneath refuse and fecal matter on the ground in order to contain the matter for removal and disposal without smashing the refuse or fecal matter in the jaws of the collection device. Another objective relates to a means for bagging the refuse and fecal matter using commonly available plastic shopping bags or specially designed pet waste bags. Yet another relates to providing a device that is collapsible (either via bending, coiling, telescoping, etc.), when not in use for convenient storage or transportation. In use, a user unfolds, extends or uncoils the shaft that extends between a handle and collection jaws, and places a plastic grocery bag, or other plastic bag in association with the jaws to secure the bag in place. The user can then place the open claw ends of the jaw e.g. claw halves, over the refuse being collected and activate the triggering mechanism of the handle to close the claw halves to encircle and encompass the waste.

Another embodiment relates to a pet waste collection tool with an integrated leash. In one such embodiment, the flexible, coiled pooper-scooper device is associated with a retractable leash.

A scoop portion attachment member is coupled to a body portion of a retractable leash, wherein the scoop portion attachment member may be either integrally connected or disengagably coupled to the body portion of the leash housing. When the scoop portion is in the closed position the curved planar regions are substantially opposed to one another to form a containment region wherein pet waste can be secured. Preferably, when the extended member is coiled and laying flat against the side of the leash housing, the jaws are maintained or retained in a closed position by a retention member, such as a clasp, so as to reduce the size of the combined leash/waste retriever device.

The present invention also relates to the field of sanitary pick-up devices for not just animal waste, but other unclean or untouchable material, trash and the like. In particular embodiments, a portable pick-up device having a storage compartment for holding a quantity of bags or wrappers is provided such that bagged pet or other waste can be transported to a convenient refuse container, toilet or sanitary area, and disposed of. Such unitary device may, for example, comprise a housing for a retractable leash, with the jaw/scoop tool associated therewith, preferably via an extendable section, like a telescoping member and/or a corrugated flexible member that renders the waste scooping features available in close approximation to the bag storage and the leash housing. A pet owner thus can leave on a walk with their pet holding a one hand-held device that provides multiple functions, including the ability to pick up waste without having to stoop or bend down and physically touch—even if only thorough a plastic bag—fresh, warm fecal matter of their pet. Similarly, it is desirable to have a clean, sanitary device for picking up unclean or untouchable material such as chemicals, solids of various kinds, small animals, specimens, temperature sensitive items, etc., in a bag or wrapper, and transporting the material or item to a convenient area, such as a refuse container, chemical bin, laboratory, etc., for deposit.

In certain embodiments, the unitary device held by a user includes not only a flexible (e.g. a member comprised of loc-line) extendable pick-up device as described herein, but also includes a supply of litter bags carried on the body of the device, such that separate bags may be withdrawn at the selection of the user.

The animal waste scooper has a preferably flexible extension that is preferably adapted to be reversibly coiled such that when it is uncoiled, the trigger operated jaws/scooping portion of the device can be employed to pick up waste and subsequently or immediately place the waste into a bag. The scooper preferably includes a handle with a trigger, an extension assembly having at least one portion thereof that has a flexible, bendable section, and a pair of jaws. Preferably such jaws are adapted to accommodate a bag such that a pet owner does not need to place their hand into a bag to recover their pet's waste.

In use, the jaws are closed by pulling on the trigger. An ordinary plastic shopping bag or other pet waste bag is opened, inverted, and placed over the jaws, the sides of the bag being retained over the jaws by adhesive, by retainer clips or any other suitable bag retention mechanism that is adapted to have the bags associated with the ends of the jaws. The jaws are then positioned over the animal waste, the trigger is pulled, and the closing the jaws enclose the animal waste in the plastic bag.

As described above, in one embodiment, the extendable waste scooping device is attached to a retractable leash housing. Preferably, separate finger or thumb operated triggers are provided to operate the brake components of the leash, with a separate trigger component provided to operate the closing of the jaw/scoop portion of the device. While one of skill in the art will appreciate the many design variations as to the number of triggers to employ to operate the various functions of such a unitary hand held device, in one embodiment, the handle of the retractable leash has the brake component positioned for operation by a user's thumb, while the scoop/jaw closing trigger is provided inside the handle portion of the leash, and is operated by an user's index finger. Thus, in one embodiment, a retractable animal leash assembly includes a housing which is carried in one hand and a leash is coiled within the housing. A brake for the leash is operable by a user's carrying hand into an activated position to hold a portion of the leash located outside said housing at a desired length. A flexible, articulated member is connected to the leash housing and is preferably coiled on the exterior of the housing so that a user can easily physically stretch out the member to an extended position such that the scoop-like jaws are positioned at a distance from the housing. A disposable bag is preferably placed over the scoop/jaw portion of the device in a manner such that the bag is retained thereon in a manner that enables the user to lower the device to the ground, where a pet deposit resides. The user then can position the open jaws—now having a bag covering such jaws—over the pet waste. Operation of the trigger then causes the jaws to close, thereby encircling the waste within the confines of the jaws, in such a manner that the bag is brought into contact and encompasses the waste. Accordingly, it is a principal object of the invention to disclose an animal waste scooper that has a flexible portion thereof, preferably a corrugated member, and most preferably one made of loc-line material, such tool adapted to pick up animal waste and to enclose the waste in plastic bags for disposal.

A scooping assembly in accordance with the present invention thus includes a pair of jaws fashioned into scoops that are adapted to encircle pet waste (e.g. with tines, teeth optional) adapted to scoop up and dispose of pet droppings and at least one triggering member operatively coupled to the jaws/scoops together to scoop up the pet droppings, with the jaws/scoops attached to flexible lengths of material that are covered by a flexible film that adds stiffness to the flexible length.

Various embodiments incorporate the use of a refuse collecting bag which is disposable after it has been filled. In preferred embodiments, two relatively movable, complemental, coacting, pick-up jaws are carried at the lower end of an elongated flexible member, preferably at least one portion thereof being corrugated and/or comprised of linked ball and socket jointed elements, and in some embodiments also telescopically adjustable into a locking length, with the jaws shaped and designed to scoop pet excrement from the ground without a user having to bend over and contact such waste via their hands. The scoop jaws are preferably designed so that it may be used in scoop-like fashion for picking up excrement, but in some embodiments, a movable and a fixed jaw construction can be employed such that the movable jaw may be used as a reverse paddle to force excrement into the scoop-like jaw. Alternatively, by holding the device in a substantially vertical position, the usual pincers-like action of the two jaws may be used for excrement pick-up purposes. In other words, the flexible nature of the extended member enables the coiling of the member for easy carrying, while in use, the member may be straightened when picking up waste, thus resembling a conventional pooper-scooper device when in pick-up mode.

Thus, certain embodiments of the present invention include a pair of jaws/scoops that are connected to and employ a flexible extension (e.g. one that can be coiled to facilitate easy carrying by the pet owner on a walk), and more preferably include the ability to have a bag placed over such jaws/scoops such that a pet owner can pick up waste without using their hand (even if such hand is inside a plastic bag). Other embodiments are directed to a retractable animal tether that includes a flexible, extendable pooper-scooper device attached thereto (or integral therewith), such combined tool comprising a hand-held support; a spool rotatably mounted on the support; a flexible cord wound on the spool; and a reversibly coiled extendable member that can be bent or straightened from an initial coiled configuration into an extended configuration, with a jaw/scoop positioned at the end of such extension.

Various embodiments the present invention are directed to a device for scooping up animal waste and sealing it in an ordinary plastic film bag. Such a device includes a flexible, extendable portion, preferably comprising a corrugated flexible tube(s) that facilitate one handed waste retrieval operation at a distance from the waste. At one end of the handle is a pair of reversibly openable and closable jaws. The closed end of a bag is releasably secured between the jaws. The open end of the bag is everted over the free edges of the jaws. The open jaws with the open bag stretched between is then placed over the waste and when the jaws/scoops are closed via operation of the trigger mechanism on the handle a the other end of the device, the waste is scooped into the bag. The edges of the bag are then removed from the jaws and preferably sealed, e.g. with a tie, adhesives, twisting, etc. A locking mechanism can be provided to keep the jaws closed until ready to dispose of the sealed bag. The opening and closing and locking of the jaws may be performed with one hand by an operator mechanism located away from the jaws. Preferably a trigger is provided that separately operates the jaws after the flexible portion is extended to reduce if not eliminate the need to stoop to reach pet waste on the ground.

Thin film polymer bags are inexpensive, somewhat resilient, impermeable to moisture and odor, and readily sealed with a twist tie. One embodiment of the present invention is directed to a method and system to encapsulate the feces in one of these bags without soiling the outer edge of the bag, while the user is at the other end of a long handle. The present invention avoids the unpleasantness and indignity to which many dog owners are now subjected when they use their bare hands inside plastic bags to grasp fresh pet manure. It is accordingly an object of the invention to provide a device for picking up animal waste that keeps the operator relatively remote from the waste during the pick-up process and that packages the waste into an ordinary inexpensive plastic film disposable bag.

In one embodiment the device of the invention comprises a pair of jaws pivotally attached to one end of an extended loc-line extension, with the device being coiled to facilitate transport by a pet owner and providing a way for such device to be carried in suitcases, purses, etc. when traveling so as to provide ready access by a pet owner to a pooper-scooper device. In such an embodiment, the jaws in the open position are fitted with a thin film plastic bag while the open end of the bag is everted over the edges of the jaws. The device is now prepared for one handed operation. To pick up the owner's dog feces, the user positions the open bag over the waste, makes jaw contact with the ground, operates the trigger of the handle to close the jaws and encloses the waste within the bag. The jaws may be locked closed to continue the walk by, for example, having the trigger remain in a position so that the jaws remain closed. In a preferred embodiment, however, the bag is sealed after or upon the closing of the jaws such that the bag is removed from the jaws and sealed, such as by a lock seal or twist tie and the sealed bag is disposed of.

Incorporated herein by reference in their entireties are the following issued patents to provide sufficient written description and enablement of the many varied handle, trigger, articulated extension members, jaw, scoop and bag associated portions and features of the present invention: U.S. Pat. Nos. 3,912,316; 7,744,136 to Waltz; U.S. Pat. No. 3,328,066 to Johnston; U.S. Pat. No. 3,617,084 to Mares; U.S. Pat. No. 5,540,470 to Lu; U.S. Pat. No. 6,796,587 to Tsou; U.S. Pat. No. 4,248,468 to Hastings; U.S. Pat. No. 7,093,869 to Jung; U.S. Pat. No. 7,695,035 to Sumner, et. al; U.S. Pat. No. 7,448,659 to Auseklis; U.S. Pat. No. 5,601,321 to Simon; U.S. Pat. No. 7,325,849 to Jones; U.S. Pat. No. 5,380,054 to Galvis; U.S. Pat. No. 5,503,442, issued to Ke-Chiang; U.S. Pat. No. 4,179,145, issued to Joe Shinsako; U.S. Pat. No. 6,062,618 to Figueroa; U.S. Pat. No. 4,878,703 to Yoshioka; U.S. Pat. No. 4,865,371 to Egberg; U.S. Pat. No. 4,272,116 to Tufte, Jr.; U.S. Pat. No. 4,186,955 to Campbell; U.S. Pat. No. 3,901,545 to Shott; U.S. Pat. No. 8,449,007 to Farmer; U.S. Pat. No. 6,845,736 to Anderson; U.S. Pat. No. 7,992,907 to DeJesus; U.S. Pat. No. 4,225,174 to Hennessy et al.; U.S. Pat. No. 6,042,155 to Lockwood and U.S. Pat. No. 5,628,537 to Kiemer.

While a standalone flexible waste scooper is one embodiment of the present invention, it is believed that many pet owners only desire to carry with them one simple multifunctional device when walking their pets. Thus, in several embodiments, a combination of pet walking tools is provided to address this desire. One aspect of the present invention is therefore directed to a portable, retractable animal leash assembly, wherein the leash line is arranged on a wind-up spool mounted to rotate in a housing carried in the hand. The assembly preferably includes a brake having brake operable by the carrying hand to stop the portion of said leash line wound off a spool at a desired length, with a brake lock mechanism being associated with the leash to lock the leash in the position momentarily determined by the brake. A flashlight feature may also be incorporated on the device, as well as a bag holder. Thus, in certain embodiments, a hand-held apparatus is provided which dispenses, retracts and locks an animal leash in a desired position. Such a device comprises a hand-held leash housing formed to include a spool and having a handle portion. The spool housing rotably mounts a spool having a length of cord wrapped thereabout with the distal end of the cord being adapted to be attached to an animal collar. A coil spring is mounted between the spool and spool housing to continuously bias the length of cord in a retracted position about the spool. A high strength locking mechanism adapted to selectively apply friction to the spool and, hence, positively prevent the cord from being dispensed or retracted from the spool is provided which is actuable by way of a trigger lever formed on the handle portion of the device. A cam actuator stop is additionally provided to permit the locking mechanism to be easily maintained in a locked orientation. The handle portion is preferably provided with a trigger mechanism that operates the jaw/scoop end of the flexible, extendable device. Such trigger is preferably separately located in the handle portion such that a user can separately operate the leash retraction mechanism and the scooper mechanism at desired times. The provision of both a retractable leash combined with a fecal retrieval tool is believed to be particularly attractive as a pet owner desires as few implements as possible to carry on a walk with their pet.

With respect to retractable leash embodiments in combination with the flexible, adjustable pooper scooper tool, the following are all incorporated herein by reference in their entireties to provide sufficient written description and enablement options of the present invention: U.S. Pat. Nos. 8,528,850; 6,148,773 to Bogdahn; U.S. Pat. No. 4,501,230 to Talo; U.S. Pat. No. D439,402 to Plewa; and U.S. Pat. No. 6,648,261 to Irving.

The specification describes a hand-held gripping device, and in particular a pet waste retrieving device, comprising a jaw portion having a pair of jaws movable relative to each other between fully clamped and fully opened positions thereof, and a handle portion spaced apart from the jaw portion by a central portion, which in some embodiments may be adjustable in length via telescoping portions slidingly moved to attain a desired length. The handle portion comprises a manually-actuatable trigger (although in other embodiments the activation of the trigger is via an electronic button) operatively connected to the jaw portion by a selectively extendible pull member at least substantially disposed within the central portion. Actuation of the trigger is operative to move the pull member to thereby selectively position the pair of jaws between the fully clamped and fully opened position thereof. The selectively extendible central portion may comprise a first tubular member and, if the device is adjustable with respect to its length, may employ rotatable locking members to reversibly lock the respective portions of the central column into a fixed position. In certain embodiments, the central portion comprises a hollow, corrugated member having alternating ridges and grooves, such member being bendable so as to attain a predetermined shape. Suitable material for use in the central column will be known by those of skill in the art, but, for example, hoses used for connecting gas appliances, such as coated, stainless steel gas connector hose is suitable for many embodiments as it reversibly bends via simple manual adjustment (or in certain embodiments, via a separate trigger element) into various desired directions and retains its bent position until further altered by the user. Alternative materials can be selected for various desired attributes, such as weight, cost, color, temperature characteristics, rigidity, corrosion resistance, electrical conductivity, water permeability, glow in the dark characteristics, etc. Thus, suitable connector material for use as the entire, or alternatively only a portion of the central portion of the gripping device, may comprise a hollow, corrugated member having alternating ridges and grooves, such member being bendable so as to attain a predetermined shape, and may be made of a variety of materials, including plastic, metal, and composites. The bendable portion of the central portion can be selectively or in a predetermined manner configured into a shape so as to facilitate easier access to a desired area, object, etc. The reversible nature of the bendable nature of the tool provides a user with the ability to adjust the angle of the distal portion of the tool to accommodate the myriad of difficult angles encountered by a user. Traditional remote access tools, which have straight and non-bending (as opposed to merely pivoting or telescoping) portions, are not able to achieve the desired remote access as provided by the present invention.

Extendable tools are typically used to interact with overhead objects that may be close or remote. For example, a fruit picker may be able to reach fruit; a janitor to replace light bulbs, and elderly person to grasp objects near their chair, tree pruners to reach certain limbs in particular orientations, etc. All of these various functions are made vastly easier by the provision of applicable forms of embodiments of the present invention as described in more detail (with respect to illustrative embodiments that one of skill in the art will appreciate transcend the particular field employed for illustrative purposes.)

In certain embodiments, at least one cord is employed that operatively connects the handle portion to the jaw portion, with such at least one cord extending through said central portion and through the hollow, corrugated member having alternating ridges and grooves. In certain embodiments, only the distal portion of the device has a segment of the hollow, corrugated member so as to limit the weight characteristics of such material as compared to the overall device. In certain embodiments, the hand-held gripping device has at least ⅔.sup.rd of said central portion comprises said corrugated member. It has been found, however, that providing ten inches of such material is sufficient for many circumstances where a user desires to perform the desired bend to facilitate reaching an object to engage with the jaws of the device. As one will appreciate, however, any length of the hollow, corrugated member having alternating ridges and grooves can be used depending upon the circumstances. Thus, while in some embodiments, substantially the entire central portion comprises such material, in other embodiments; one or more sections of the central portion comprise such a hollow, corrugated member. In certain preferred embodiments, the distal portion has at least 1 inch of such hollow, corrugated member, more preferably at least about 3 inches of such material, and most preferably at least about 6 inches of such material. In other embodiments, at least two portions of the central column have sections with such hollow, corrugated member such that a user can preposition each section for a desired bent configuration, thus permitting the ability to reach an object remote form the user that may be difficult or impossible to reach using traditional gripper devices with straight central columns.

In certain embodiments, the hand-held gripping device employs a handle portion that has a second manually-actuatable trigger, with such second trigger able to adjust the orientation of the distally positioned jaw portion by effecting a change in the shape of the one or more corrugated members along the extent of the central portion. In some embodiments, the trigger that functions to alter the bending of the corrugated member is a rotatable knob, such that many varied angular orientations of the distal end (with the jaws) can be attained via rotation of a knob positioned near or on the hand grip of the device. Electronic means can also be employed for such purpose, as well as for the operation of the jaws between their closed and open positions.

While certain embodiments solely employ at least one section of a corrugated member to achieve desired bendable characteristics, other embodiments of the hand-held gripping device have a portion of said central portion that is in telescoping relationship with an adjacent portion of said central portion. Telescoping shafts may have two or more shaft members so long as each inner member is slightly smaller in cross-sectional area than the next outer member. In such embodiments, a locking member associated with said central portion is used to fix two adjacent members of said central portion in an engaged position, with the locking member operable between a first locking position and a second unlocking position. The locking member may comprise a coupling member, such as rotatable collar that can be manipulated by a user to adjust the griping member's length. In one embodiment, a section of corrugated hollow material is positioned at the distal end of the device, about 3 to 6 inches away from the jaws (and in the direction of the hand grip) and two adjacent members of the central column portion are operatively associated with each other in a slidingly telescoping relationship with a locking member is associated with at least one of said two adjacent members, the locking member comprising a selectively radially expandable mandrel radially expanded into engagement with the adjacent members to permit the length of the central column member to be varied.

In preferred embodiments, a pull member comprises first and second pull rods and a cam body supporting a cam is used, with the pull rods associated with the cam support body. The cam is characterized by a first, engaged condition in which the cam is in contact with the second pull rod to thereby fix the length of the pull member, and a second, disengaged condition in which the cam is out of contact with the second pull rod to thereby permit the length of the pull member to be varied. The user-actuatable trigger comprises a manually operable release trigger provided on the handle portion, which is, operatively connected to the cam via a connecting rod.

One of skill in the art, especially guided by the incorporated references, will appreciate the varied types and features of gripping devices that can be constructed and that further incorporate the hollow corrugated member(s) as described herein in order to attain desired bendable capabilities of a particular user. For example, and without limitation, the present invention can be employed in a variety of fields where the problem of access around otherwise difficult angular orientations is presented, such fields including but not limited to the following: fruit pickers; janitors replacing light bulbs, elderly persons grasp objects near their chair, tree pruners; surgeons and dentists/orthodontists to reach interior portions of a person's anatomy, etc.

While preferably the bendable portion of the central column is made of a corrugated material (due to its ability to remain open in its central internal core, thus permitting pull cords to operate therein), those of skill in the art will appreciate that—especially dependent upon how severe and desired bending may be—that other types of bendable segments can be employed to achieve such a function. For example, pliable plastic or rubber-type sections can also be alternatively or in conjunction employed on a gripper device of the present invention so as to achieve the ability of a user to reach objects that would be difficult or nearly impossible using a device having a straight and non-bendable column. Of course, the ability of such a section to uphold the weight of the jaws, especially after the jaws have grasped some desired object, is an important consideration when selecting appropriate materials to employ for the bendable portion of the column. In other words, a sufficient amount of rigidity and/or operational integrity of the central column is required for most applications.

In still other embodiments of the present invention, one or more springs can be employed (with such spring(s) having desired structural integrity with respect to an ability to bend, an ability to support weight that may be encountered when the jaws engage an object and the device is lifted in the air, etc). Thus, in one embodiment, a section of spring is used along the central portion of the device with a cord mechanism that is attached to the jaw end of the device, such that when the cord is pulled, the spring section bends to angularly adjust the jaws such that they can reach around corners otherwise inaccessible with a straight column gripper device.

To comply with appropriate written description and enablement requirements and to provide sufficient guidance in how one of skill in the art can make and use the various and numerous embodiments of the present invention, incorporated herein in their entireties are the following: Hsu, U.S. Pat. Nos. 6,513,844; 6,520,556, 6,739,637, and 4,669,769 to Polder, Jr; U.S. Pat. No. 4,962,957 to Traber; U.S. Pat. No. 8,061,751 to Hatcher; U.S. Pat. No. 7,934,756 to Kroeze; U.S. Pat. No. 8,061,751 to Hatcher; U.S. Pat. No. 7,665,782 to Buzby et al.; U.S. Pat. No. 8,091,936 to Graziano; U.S. Pat. No. 7,980,609 to Khubani; U.S. Pat. No. 5,895,082 to Kaluzny; U.S. Pat. No. 5,590,923 to Berger et al.; as well as U.S. Pat. No. 4,962,957; U.S. Pat. No. 4,709,839; U.S. Pat. No. 3,527,492; U.S. Pat. No. 4,613,179; U.S. Pat. No. 4,669,769; U.S. Pat. No. 6,257,634; U.S. Pat. No. 7,004,520; U.S. Pat. No. 6,513,844; U.S. Pat. Nos. 6,571,479; 6,042,155 and U.S. Pat. No. 6,848,731.

Some extendable tools have fixed tool heads, e.g. a dust mop, or a flexible tool head, e.g. a device for swapping out light bulbs that has spring-like fingers. Other extendable tools include a hand powered actuatable tool head assembly having movable elements, such as, but not limited to, a tree pruner. In other embodiments, extendable tools have an actuatable tool head assembly that have drive assemblies in order to allow the user at the bottom end of the extendable tool to actuate the tool head at the upper end of the extendable tool. While an actuatable tool head assembly associated with one end of an extended tool may be any type of tool, and while the present discussion relates in particular to a tool having a jaw assembly as an example, more specifically a reaching tool that may be used to grip objects between the two jaws, it will be understood by those of skill in the art that various known tool head assemblies can supplant the discussion of clasping jaws and thus, will otherwise suffice to describe the novel and non-obvious aspects of the present invention in such other embodiments and functions.

Thus, as opposed to the prior art, where materials employed for the central column were hardened plastic polymers or any of substantially non-malleable metals, the present invention can be seen as distinctly different as it relates to employing materials and constructions that bend or otherwise flexible so as to achieve the functional attributes that the prior art devices cannot achieve.

Other embodiments, have a more ball-cupping jaw/claw portion and when uncoiled, can be extended a great extent (over 10 feet, etc.) so that a golfer is able to easily retrieve balls hit into the water or rough. In still other embodiments, one device having the handle 40, trigger 41 and flexible central portion 30, is adapted to have replaceable and disenagagable distal end portions such that a user can achieve a myriad of different desired operations simply by removing and replacing end tools that have complementary detachable housings associated therewith that interact and reversibly connect to the non-handle end of the tool.

One will appreciate that this summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, pictures, etc. will provide a basis for the scope of the present invention as it may be claimed now and in future applications.

BRIEF DESCRIPTION OF THE DRAWINGS

Other advantages of the present invention will be readily appreciated as the same becomes better understood by reference to the following detailed description when considered with the accompanying drawings, wherein:

FIG. 1 is a lateral perspective view of an extendible gripping device according to the present invention;

FIG. 2 is another view of one embodiment showing the corrugated section(s) of the central column near the jaw portion of the inventive gripping device and toward the handle portion of the device.

FIG. 4 is a perspective view showing another embodiment with a corrugated segment in addition to a telescoping locking member along the central column.

FIG. 5, shows a perspective view of an embodiment where substantially the entire length of the central column comprises a corrugated segment.

FIG. 6 shows how the corrugated segment can be bent into configurations, including winding the central column around so that the device can be stored and transported easily.

WRITTEN DESCRIPTION OF CERTAIN PREFERRED EMBODIMENTS

Figure 3:
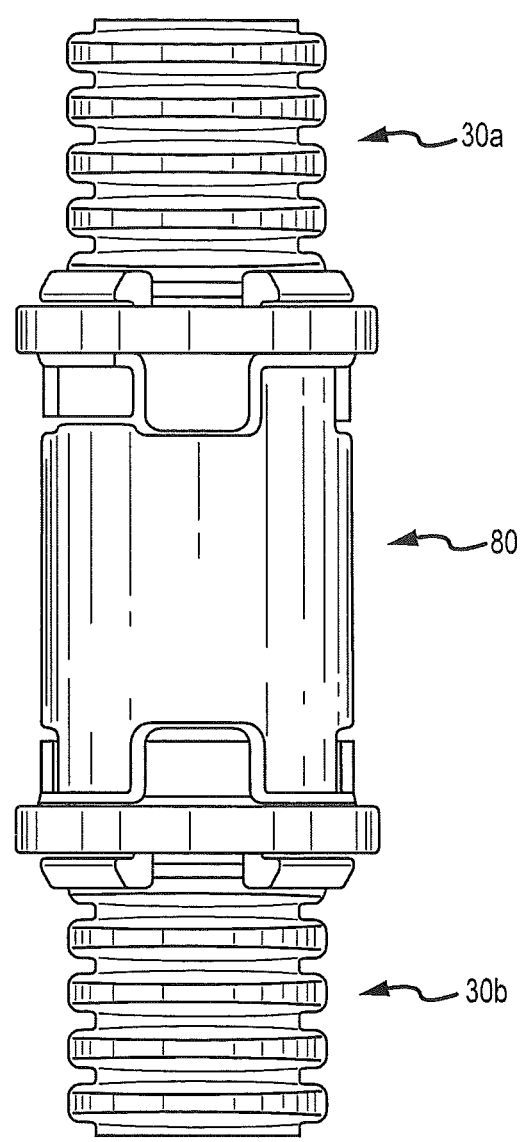
FIG. 3 comprises a perspective close-up view of one embodiment of a corrugated section of the column, showing a dissociable coupling.

It will be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention. For the following description, the actuatable tool head assembly is described as a gripper having a jaw assembly 11. It is understood, however, that any type of actuatable tool head assembly may be used.

As disclosed in the figures, various embodiments of the present invention generally comprise a hand-held gripping device having a jaw portion (indicated generally at 10) comprising a pair of jaws 11a, 11b and a handle portion (indicated generally at 40) spaced apart by a selectively extendible central portion (indicated generally at 70). The handle portion 40 comprises a manually-actuatable trigger 41 operatively connected to the jaws of the jaw portion by a pull member. Actuation of the trigger 41 is operative to move the pull member to thereby selectively position the pair of jaws 11a, 11b between fully clamped and fully opened positions thereof. It will be understood that the jaw construction and the handle portion construction is intended as exemplary only, and that those of skill in the art will appreciate how to adapt such portions as desired, consistent only with facilitating operation of the bendable column gripping device as hereinafter described.

A pull member is interconnected with the jaw and handle portions such that manual actuation of the trigger 41 effects movement of the jaws 11a, 11b.

In certain embodiments, the user-actuatable release trigger 41 of the present invention comprises a release button 42 disposed on the trigger 41 of the handle portion 40. In the event that the distance between the jaw portion 11 and the handle portion 40 is not appropriate in light of the task contemplated by the user, the user may adjust the length of the central portion by first unscrewing a collet assembly 80 to thus permit telescoping movement of first and second tubular members. The user next actuates the release trigger, either by depressing the release button or turning the collar (depending on the form of the invention), which actions cause the second coupling to move from the engaged to the disengaged position. At this point, the pull member may be lengthened or shortened concurrently with telescoping movement of the first and second tubular members. Thus, while depressing the release trigger 42, the user grasps the second tubular member and changes the distance between the handle portion and the gripping portion as desired. After the desired length is obtained, the user releases release trigger and tightens the collet assembly to thereby fix the lengths of each of the central portion and the pull member.

Selective positioning of the first and second tubular members may be effected by rotational movement of one of the first or second tubular members of the central portion.

In certain embodiments, the gripping device of this embodiment comprises a selectively extendible central portion 70 including a first tubular member 71 slidingly telescopingly received within a second, larger-diameter tubular member 73. In order to fix the relative positions of the first 71 and second 73 tubular members, there is provided a collet assembly 80.

A locking mechanism 42 may be provided to fix the pivotal position of the trigger 41, and thereby fix the relative positions of the jaws 11 between the fully open and fully closed positions thereof.

In operation, from the position wherein the jaws 11 are fully opened, a user manually depresses trigger 41 to retract the pull rod 50 and thereby move the jaws 11 toward each other.

To understand and appreciate the varied and numerous applications of the present invention in the context of tools that do not employ the gripping jaw device used as an illustrative example herein, the inventors incorporate by reference herein, in their entireties, the following patents to provide the detailed embodiments that, with the features here described, facilitate far easier access to previously difficult to reach areas so that the various functional assemblies at the remote end of a tool can be used effectively: Hsu, U.S. Pat. Nos. 6,513,844, 6,520,556, and 6,739,637, 4,669,769 to Polder, Jr; U.S. Pat. No. 4,962,957 to Traber; U.S. Pat. No. 8,061,751 to Hatcher; U.S. Pat. No. 7,934,756 to Kroeze; U.S. Pat. No. 8,061,751 to Hatcher; U.S. Pat. No. 7,665,782 to Buzby et al.; U.S. Pat. No. 8,091,936 to Graziano; U.S. Pat. No. 7,980,609 to Khubani; U.S. Pat. No. 5,895,082 to Kaluzny; U.S. Pat. No. 5,590,923 to Berger et al.; as well as U.S. Pat. No. 4,962,957 to Tucker; U.S. Pat. No. 4,709,839; U.S. Pat. No. 3,527,492 to Hollis; U.S. Pat. No. 4,613,179 to van Zelm; U.S. Pat. No. 4,669,769 to Polder; U.S. Pat. No. 6,257,634 to Wei; U.S. Pat. No. 7,004,520 to Khubani; U.S. Pat. No. 6,513,844 to Hsu; U.S. Pat. No. 6,571,479 to Wu; and U.S. Pat. No. 6,848,731 to Khubani.

It will be appreciated from the above disclosure that the present invention improves upon the prior art by providing a bendable gripping device that is robust yet simple in design, and that allows easy adjustment of the direction of the jaws 11 to reach around tight corners or other places where a straight columned device would simply not function to retrieve desired objects remote form the user.

In one embodiment, a hand held gripping device is provided that has a jaw portion comprising a pair of jaws 11 that are movable relative to each other between fully clamped and fully open positions. A handle portion 40 is spaced apart from the jaw portion 11 by a selectively extendable portion, the handle portion having a manually actuable trigger connected to the jaw portion. An extendable pole member, preferably running longitudinally through a tubular section, operatively connecting the jaw portion 11 to the handle portion 40, is provided. Actuation of the trigger 41 is therefore operative to move the pole member to selectively position the pair of jaws 11 between fully clamped and fully opened positions. Between the jaw portion 11 and the handle portion 40 is therefore a central portion, preferably comprising a hollow, corrugated member 30. Such corrugated member 30 preferably has alternating ridges and grooves such that the central portion of the device is able to bend in order to attain predetermined shapes. In particular embodiments, at least one cord is connected between the handle portion and the jaw portion 11, such that the cord extends through the central portion of the device.

As illustrated in FIG. 2, in certain embodiments of the present invention, two or more corrugated members 30a and 30b are provided at different relative locations along the device, and more specifically along the central portion of the device. In preferred embodiments, at least two thirds of the central portion comprises the corrugated member 30. In still other embodiments, at least a central portion of the device is in a telescoping relationship with an adjacent portion of the device, namely, a first portion 71 is telescopically related to a second portion 73, with a locking member 80, preferably a locking collar, associated with a central portion. The locking member 80 is provided in a fashion so that the two adjacent members of the central portion 71, 73 may be in an engaged position such that the lengthy of the central portion 70 can be effectively adjusted by the user. The locking member 80 can alternatively be referred to as a coupling member between the two portions 71 and 73. In a preferred embodiment, the locking member 80 comprises a selectively radially expandable mandrel.

In other embodiments, a user actuable trigger 41 comprises two operable triggers with the operation of a first trigger 41 causes the reversal opening and closing of the jaws 11, whereas the other trigger (not shown) causes the distal end of the device to move such that the distal end bends in relationship to the longitudinal axis of the device.

In other embodiments, a selective positioning of a knob (not shown), such knob position near the trigger/handle portion of the device, is provided in order to cause rotational movement of the distal end of the device through manual adjustment of the knob.

In still other embodiments (for example, FIG. 5) the majority of the portion between the handle portion and the jaw portion comprises corrugated material 30. In such an embodiment, a locking member 80 can be employed, so as to selectively adjust the length of the device in a telescoping relationship, even though the telescoping members themselves are made of a corrugated, bendable material. In other embodiments, however, the locking member 80 can be dispensed with, and the corrugated member 30 can comprise the entirety of the portion between the handle portion 40 and the jaw portion 11 of the device. In such embodiments, it is possible to compress the device in a coiled manner, making transportation and storage of such a device far easier. For example, the bendable nature of the corrugated members 30 used with the device can be employed in order to compact the device to fit within luggage, purses, etc., that may be carried by individuals, especially elderly individuals in need of such a compact, adjustable device.

Figure 7:
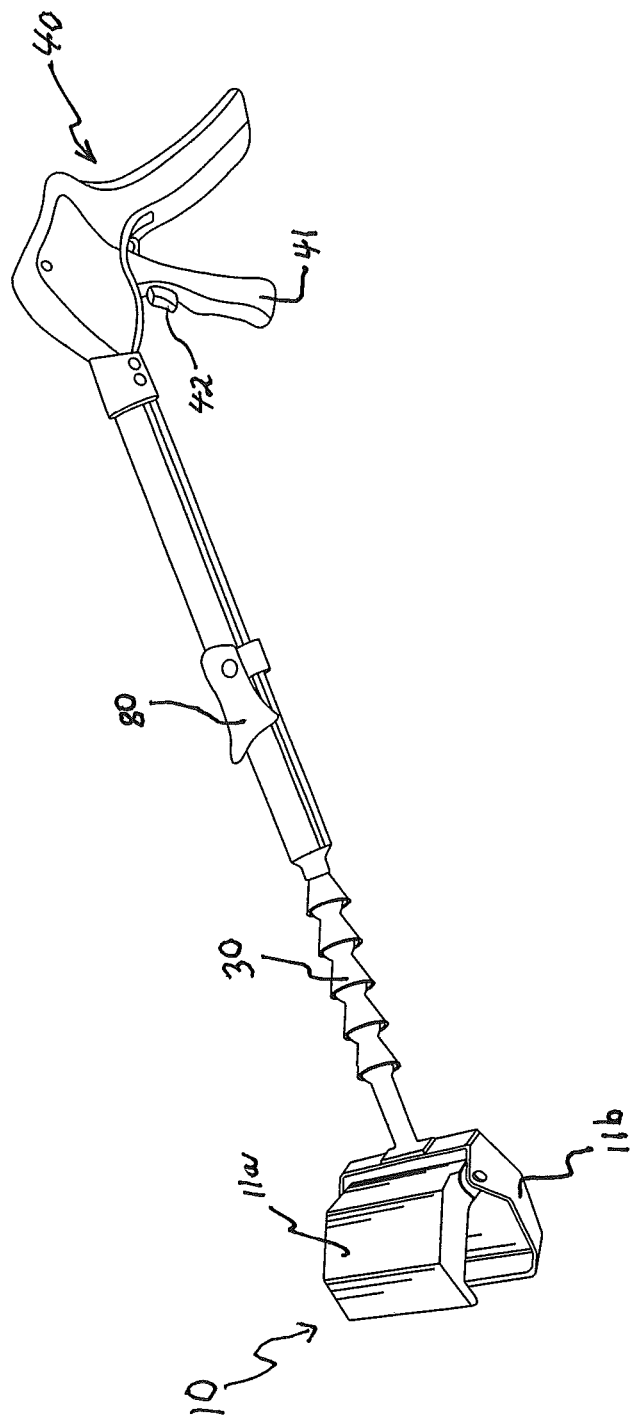
FIG. 7 is a perspective view of an animal waste scooper according to the present invention showing at least one portion of articulated members and an adjustable telescoping mechanism.
Figure 8:
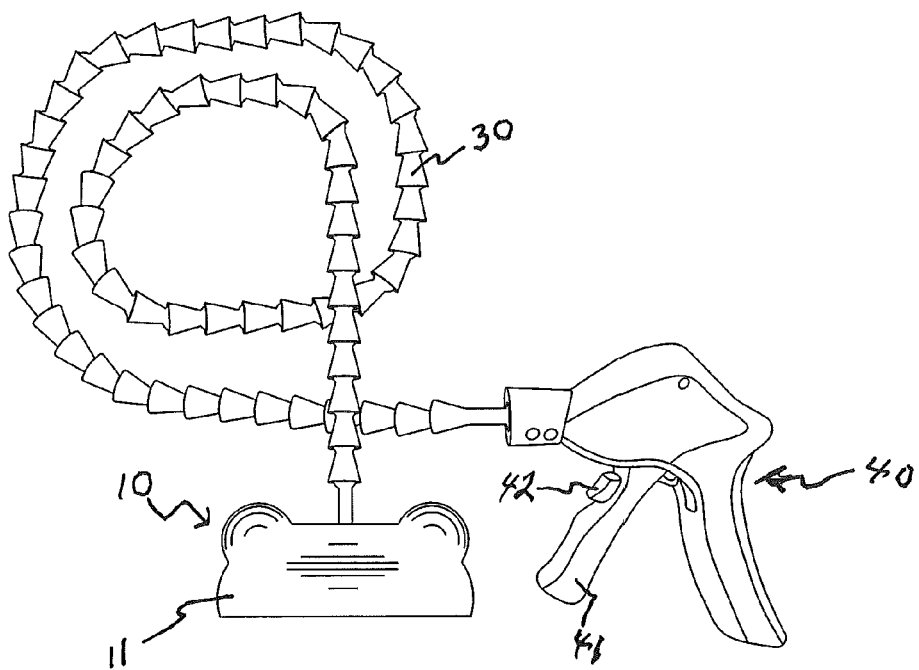
FIG. 8 is an illustration of an animal waste scooper embodiment with a bendable loc-line type flexible extension and stylized jaw portion shaped as a partial dog-bone.
Figure 9:
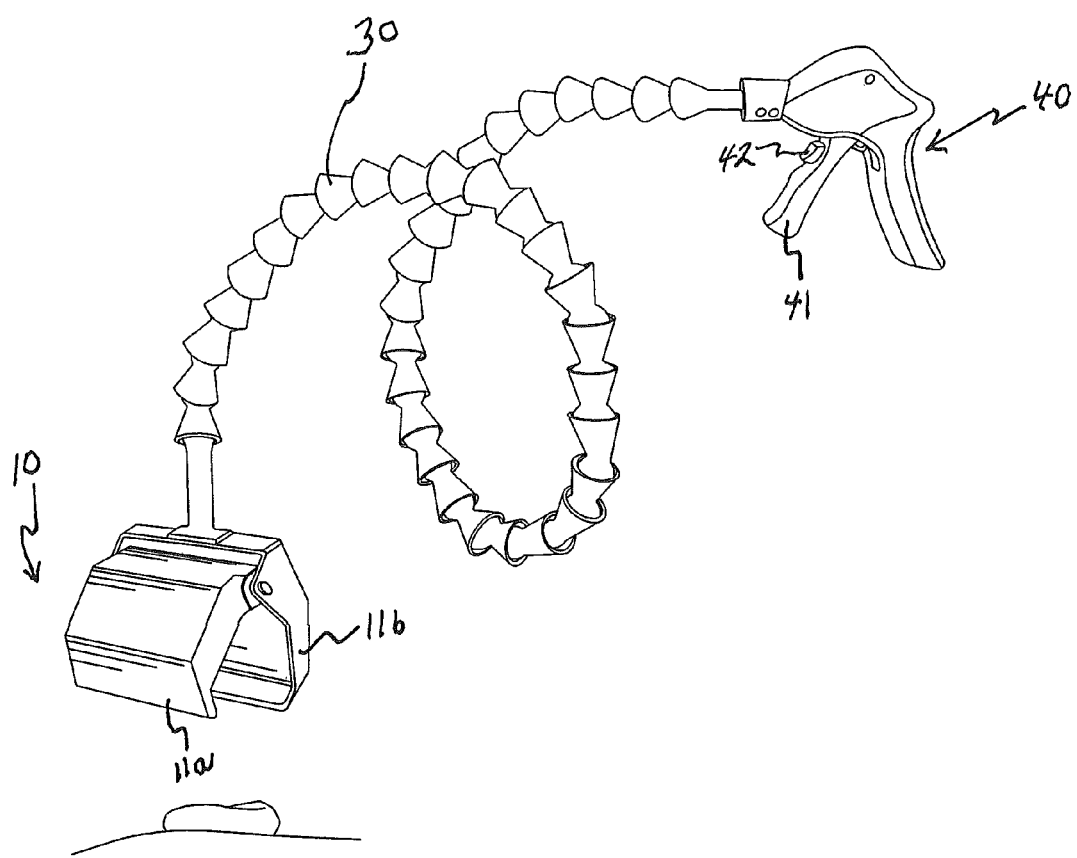
FIG. 9 is an illustration of a further embodiment with another type of jaw/claw scoop member associated with an articulated, bendable central portion.
Figure 10:
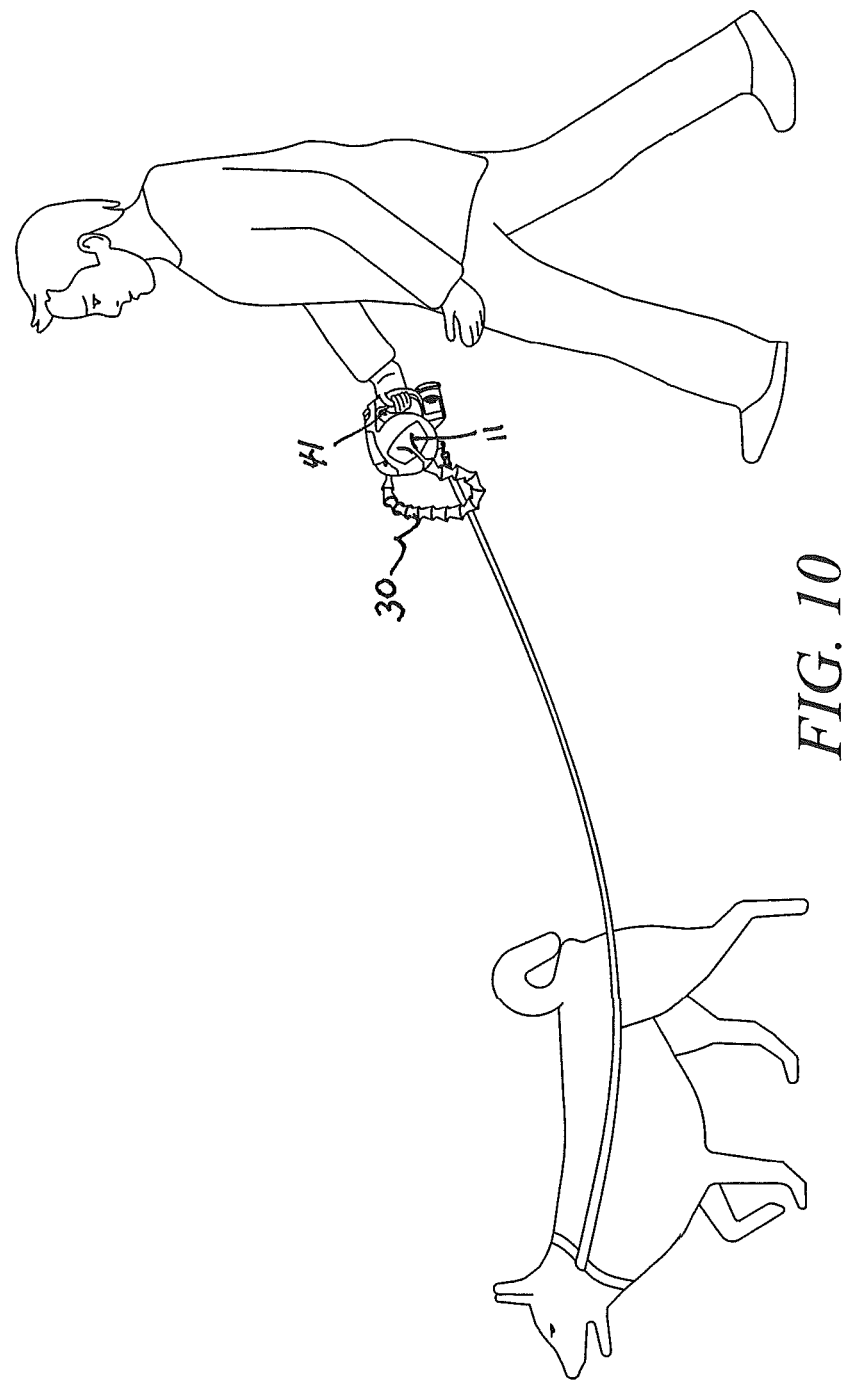
FIG. 10 is an illustration of a pet owner and pet with a retractable leash, flashlight, bag receptacle and flexible waste scooper combination.
Figure 11:
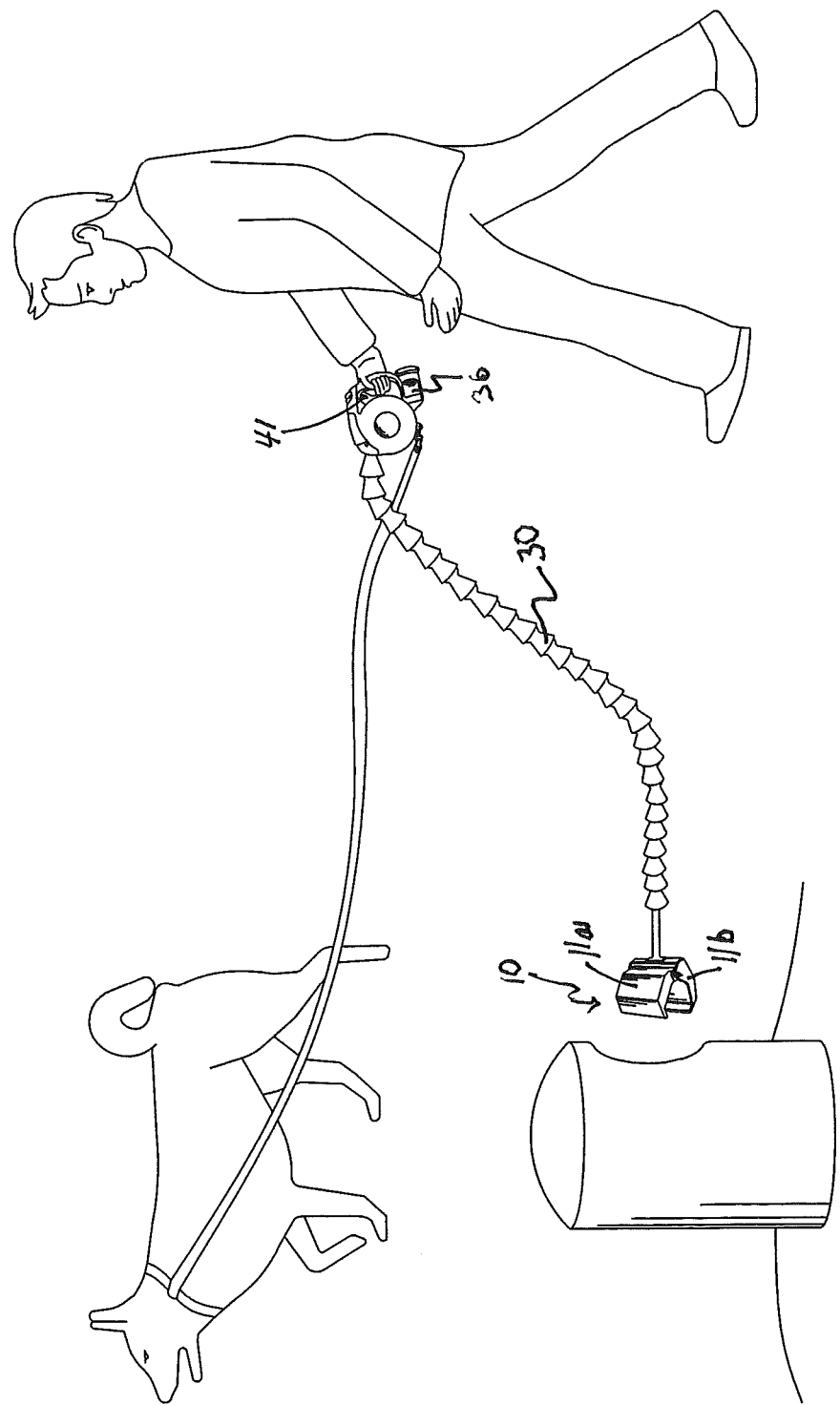
FIG. 11 is an illustration of the device of FIG. 10 where the animal waste jaw/claw is in an extended, unwound configuration amenable to depositing waste in a trash receptacle.
Figure 12A:
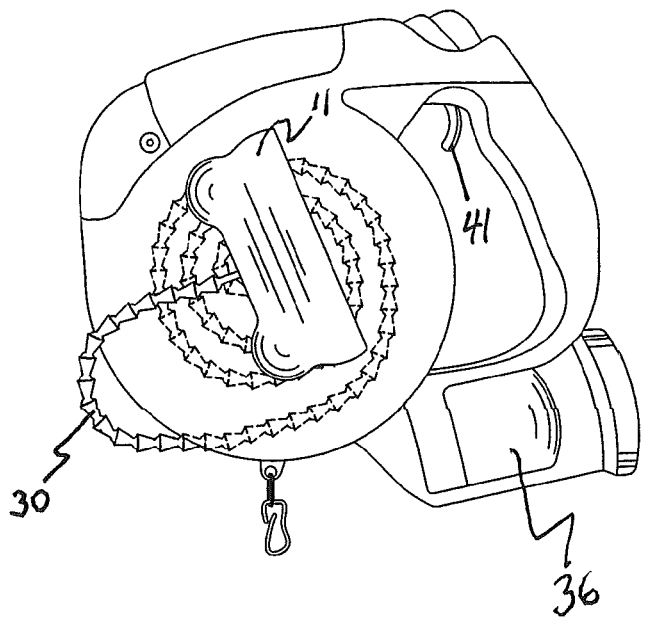
FIG. 12A shows one embodiment of the present invention where the central portion is coiled and the jaw/claw portion is positioned close to a retractable leash housing having a trigger that operates the jaw/claw mechanism.
Figure 12B:
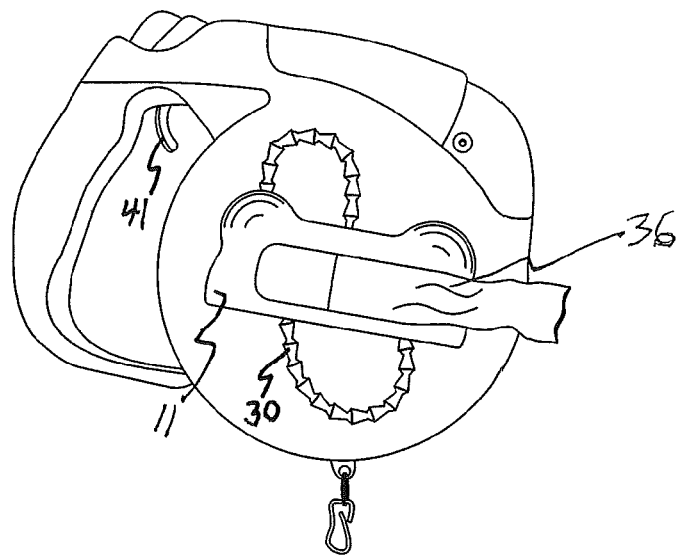
FIG. 12B shows another embodiment of the present invention with a shorter flexible central portion connected to a partial dog-bone stylized jaw portion having a waste bag receptacle as part of one of the jaw/claw members.

As described above and herein, various embodiments of the present invention are directed to so-called "pooper-scooper" type devices, with the advantage being that a pet owner can more easily carry and transport such a device due to the various flexibility, bendability and adjustability characteristics of the many versions of the present inventions. Thus, FIGS. 7-12B illustrate such embodiments. FIG. 7 is a perspective view of an animal waste scooper according to the present invention showing at least one portion of articulated members and an adjustable telescoping mechanism. FIG. 8 is an illustration of an animal waste scooper embodiment with a bendable loc-line type flexible extension 30 and stylized jaw portion 11 shaped as a partial dog-bone. FIG. 9 is an illustration of a further embodiment with another type of jaw/claw scoop member 11 associated with an articulated, bendable central portion 30. FIG. 10 is an illustration of a pet owner and pet with a retractable leash, flashlight, bag receptacle and flexible waste scooper combination. FIG. 11 is an illustration of the device of FIG. 10 where the animal waste jaw/claw is in an extended, unwound configuration amenable to depositing waste in a trash receptacle. FIG. 12A shows one embodiment of the present invention where the central portion is coiled 30 and the jaw/claw portion 11 is positioned close to a retractable leash housing having a trigger 41 that operates the jaw/claw mechanism 11. FIG. 12B shows another embodiment of the present invention with a shorter flexible central portion 30 connected to a partial dog-bone stylized jaw portion 11 having a waste bag receptacle 36 as part of one of the jaw/claw members.

In certain embodiments, including the movable jaws embodiments in FIG. 1-6, the animal waste embodiments of FIGS. 7-12 and the golf embodiments of 13-17, an objective is to provide a gripping device including a locking mechanism 42 for locking the gripping jaws, claws, ball-grasping members, 11 etc. in a holding or grasping or gripping position. Thus, in certain embodiments a device is provided that includes a handle body, a hand grip 40 secured to the handle body having a trigger 41 connected to a cord that extends through a flexible corridor 30, preferably one that is corrugated, and more preferably constructed of loc-line elements linked together, at least one gripping jaw or claw 11 movable via manipulation of the trigger 41, and a locking mechanism 42 for locking the jaw or claw 11 into a closed position. The locking mechanism 42 may include, for example, a pawl rotatably secured to a hand grip and having a first end for engaging with the handle body, the handle body including a plurality of teeth formed therein with the pawl including teeth for engaging with the teeth of the handle body. One of skill in the art, however, will appreciate the varied other locking devices that can supplant the pawl/teeth design of locking mechanisms that can be employed with the present invention.

In more general embodiments, the present invention is directed to a hand-held reacher for gripping an object and includes a handle portion 40, a jaw portion 10, and a shaft extending between the handle portion and the jaw portion, with such extended portion including at least one section that is flexible 30, preferably corrugated and most preferably constructed of loc-line-type articulated joints that have hollow interiors to facilitate a cord extending through the interior of the flexible corridor formed. At one end of such a device there is at least one jaw/claw portion 11 having at least one of the jaws 11 moveable between an open position and a closed position, and the handle portion 40 having a manually-operable trigger 41 for moving the jaws 11 between the open and closed position. An additional locking member 42 for releasably locking the jaws in a closed or partially closed position is also a feature of preferred embodiments.

In still other embodiments, the present invention is directed to a hand-held gripping device having a jaw portion 10 that includes a pair of jaws 11 movable relative to each other between fully clamped and fully opened positions. A handle portion 40 is spaced apart from the jaw portion 10 by a selectively extendible central portion, with the handle portion including a first manually-actuatable trigger 41 operatively connected to the jaw portion 10 by a selectively extendible pull member at least substantially disposed within the bendable, preferably corrugated central portion 30. Actuation of the trigger 41 is operative to move the pull member to thereby selectively position the pair of jaws 11 between the fully clamped and fully opened positions. The central portion can be constructed of various materials, including ball-and-socket connectable members of varying lengths, diameters, etc, with such members having a hollow, interior through which a cord or wire can extend through, thus connecting a handle portion 41 to a movable jaw portion 10 of a device. Preferably such a corrugated member 30 has alternating ridges and grooves, which may be covered by an outer sheath of preferably flexible material, such as rubber, fabric or plastic, with the corrugated member 30 being bendable so as to attain a predetermined shape.

In preferred embodiments, the corrugated member 30 is made of loc-line connected elements that have ball and socket connections that permit substantial flexibility of a connected length thereof. A pull member, such as at least one cord, is operatively connected to the handle portion 40 at one end and to the jaw portion at another end of the device. The cord extends through and is preferably entirely encompassed by the central portion. The corrugated member 30 has a first configuration whereby prior to actuation of the actuation trigger 41, the pair of jaws 11 is in the fully opened position and the corrugated member is bent. A locking member 80 may be operatively associated with the central portion so that two adjacent members of the central portion can be moved with respect to each other in a slidingly telescoping relationship and can then be locked into place. The locking member 80 may be a selectively radially expandable mandrel, radially expanded into engagement with the adjacent members to permit the length of the pull member to be varied. The corrugated member 30 is preferably constructed of plastic and is able to be bendable so as to attain a predetermined shape.

In certain embodiments, at least two portions of the central portion column are made of hollow, corrugated members 30 such that a user can preposition each of the portions for a desired bent configuration. The central portion comprises at least 6 inches of the hollow, corrugated member 30 and two or more corrugated members may be provided at different relative locations along the central portion of the device. Preferably, at least two thirds of the central portion comprises the bendable portion that is adapted to be coiled to facilitate transportation and storage, and further includes a locking member operable between a first locking position and a second unlocking position. The actuatable trigger 41 preferably includes a manually operable release trigger 41. The central portion in certain embodiments also includes a bendable portion made of rubber.

One particular aspect of the present invention is directed to the playing of golf. Playing golf requires that the golfer is able to pick the ball up from, and place the ball on to the playing surface, and further requires the ability to tee up a golf ball. The teeing, placement and collection of balls from the ground normally requires that the golfer bends, which can be challenging for disabled or elderly players. Thus certain embodiments of the present invention are directed to a golf ball retriever device, while others are directed to grasping a golf ball and preferably also an associated golf tee, such that the ball and the tee can be planted into the ground so that a golfer can tee off. The present invention thus provides a way for a golfer to avoid having to bend down to place his/her teed ball, thus being of considerable benefit to old golfers and those with bad backs or having limited flexibility.

Figure 13:
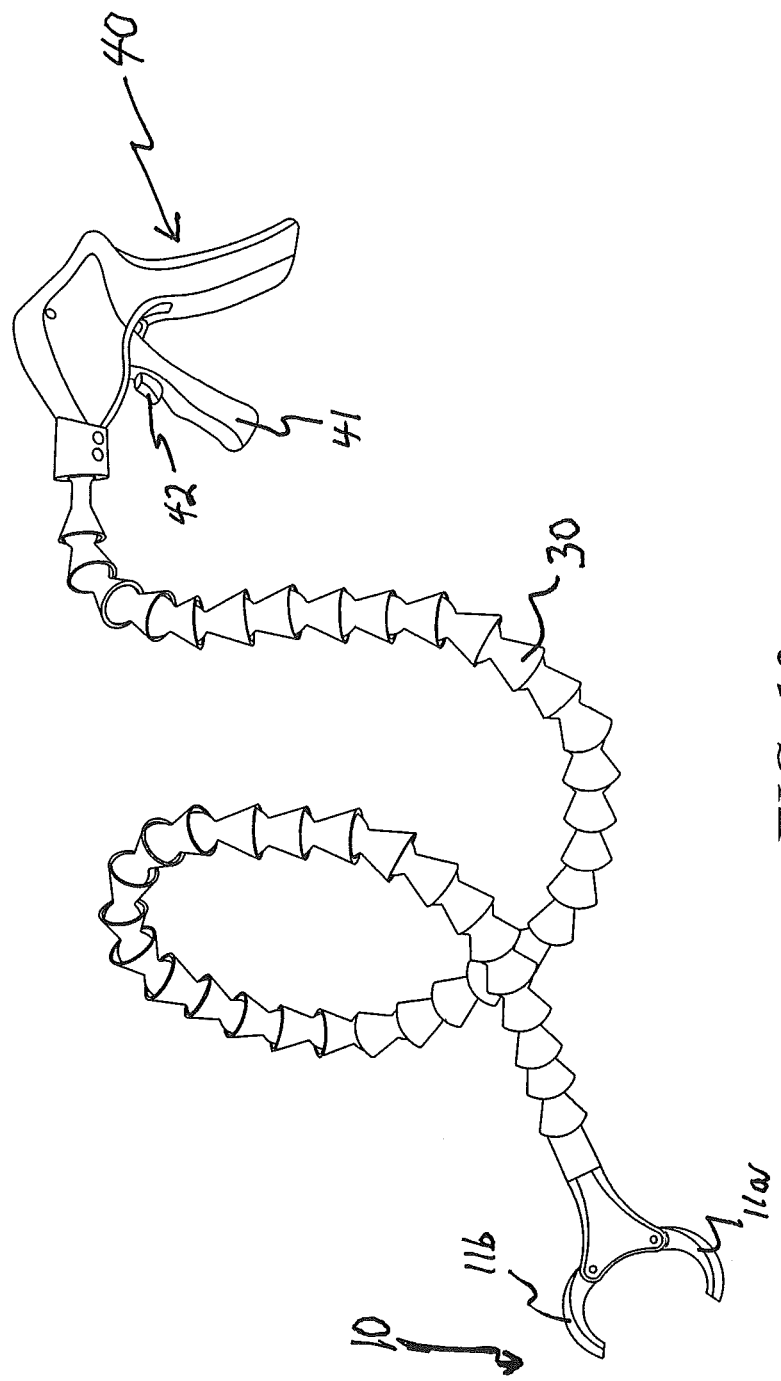
FIG. 13 shows yet another embodiment of the present invention where the claw portion is adapted to encircle a golf ball and golf tee, with the flexible central portion able to be extended into a linear configuration to enable a golfer to plant the ball/tee into the ground.
Figure 14:
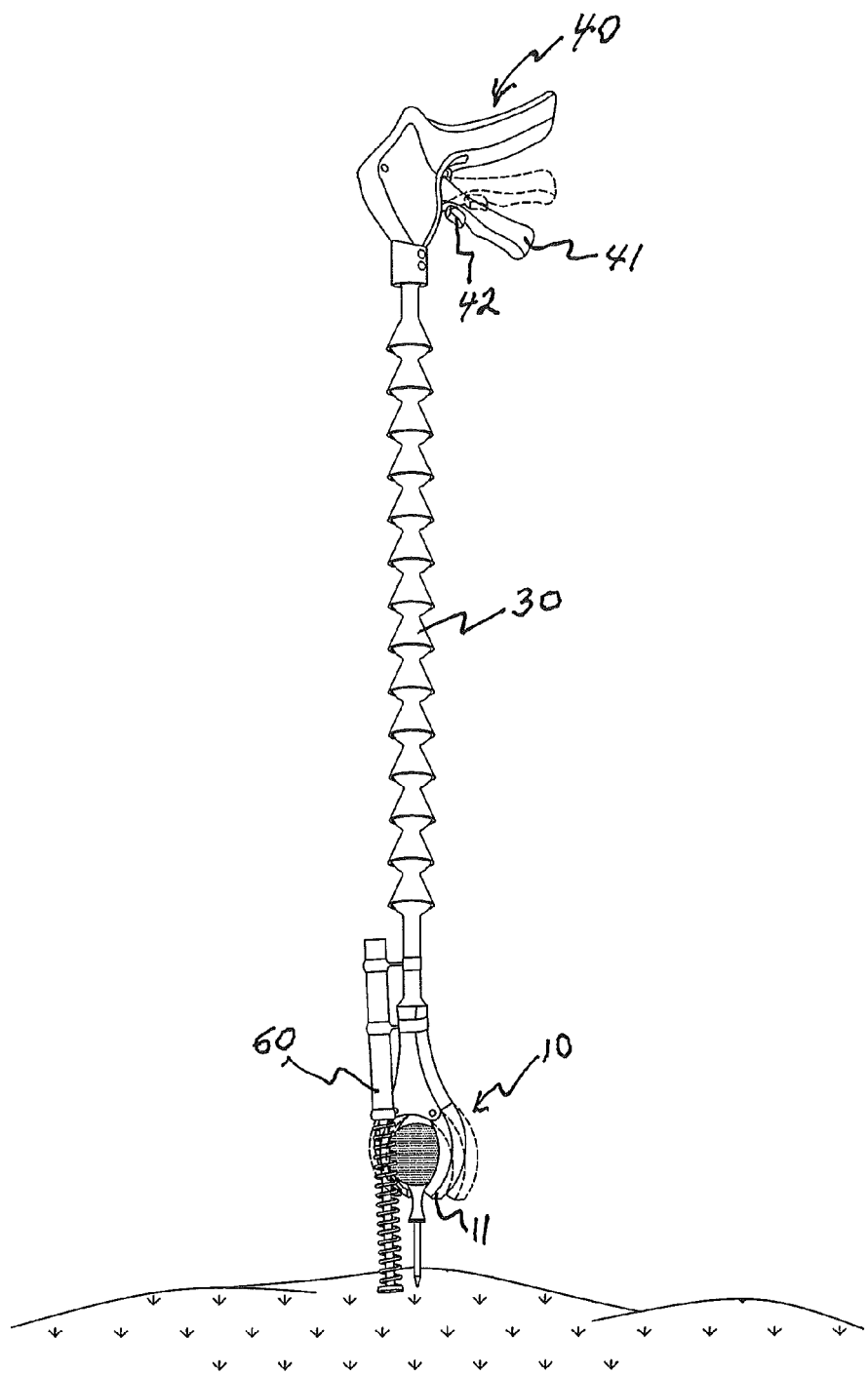
FIG. 14 shows an embodiment of the present invention where the flexible central portion assumes a linear configuration to facilitate teeing of a ball, with a stabilizing pogo-stick type member associated with the lower portion of the device.
Figure 15:
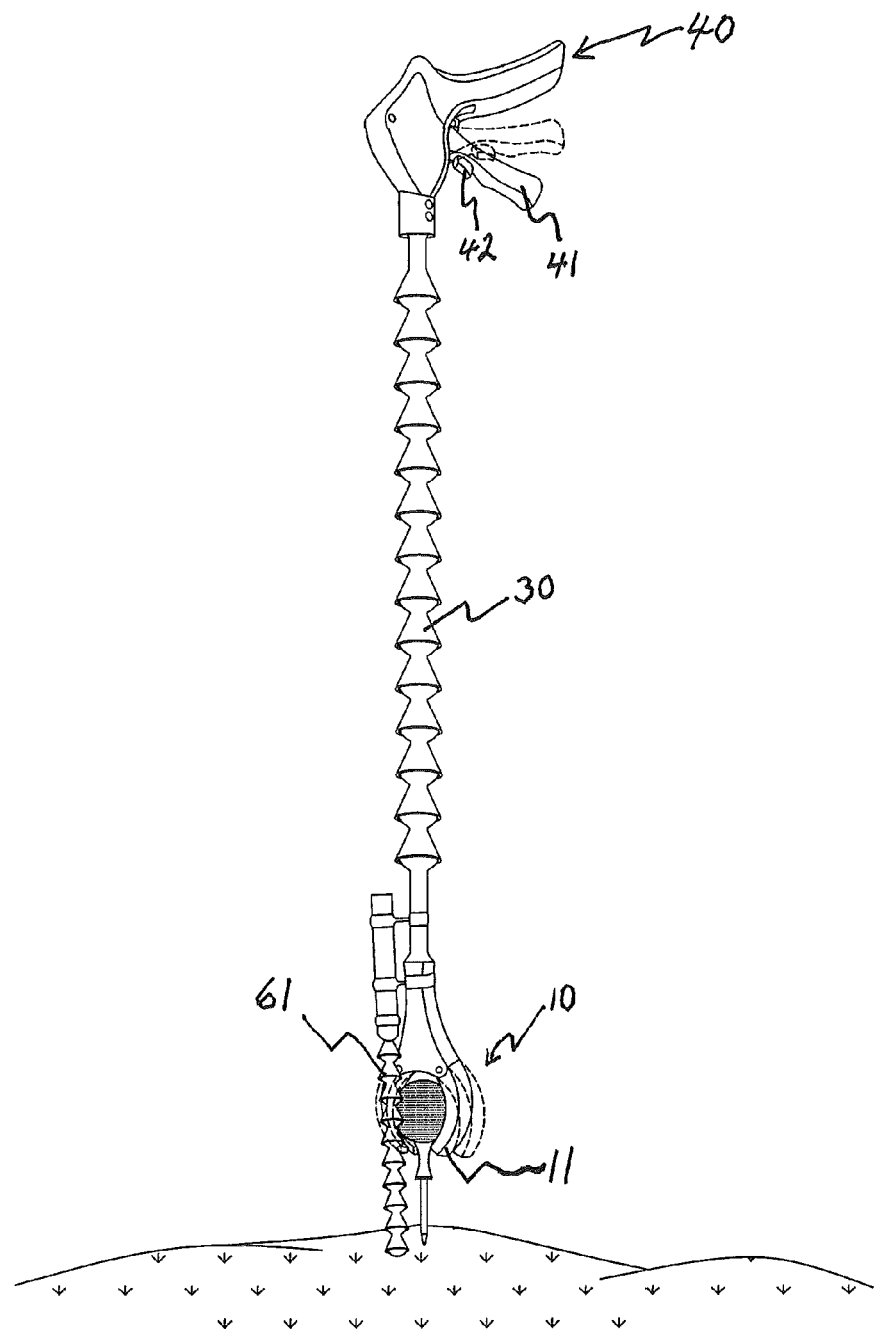
FIG. 15 shows a further embodiment of the present invention where a separate articulated member provides stability for the teeing operation, with the shorter articulated arm designed to bend when contacted with the ground as the tee is forced downwardly by a golfer pressing down on the handle.
Figure 16:
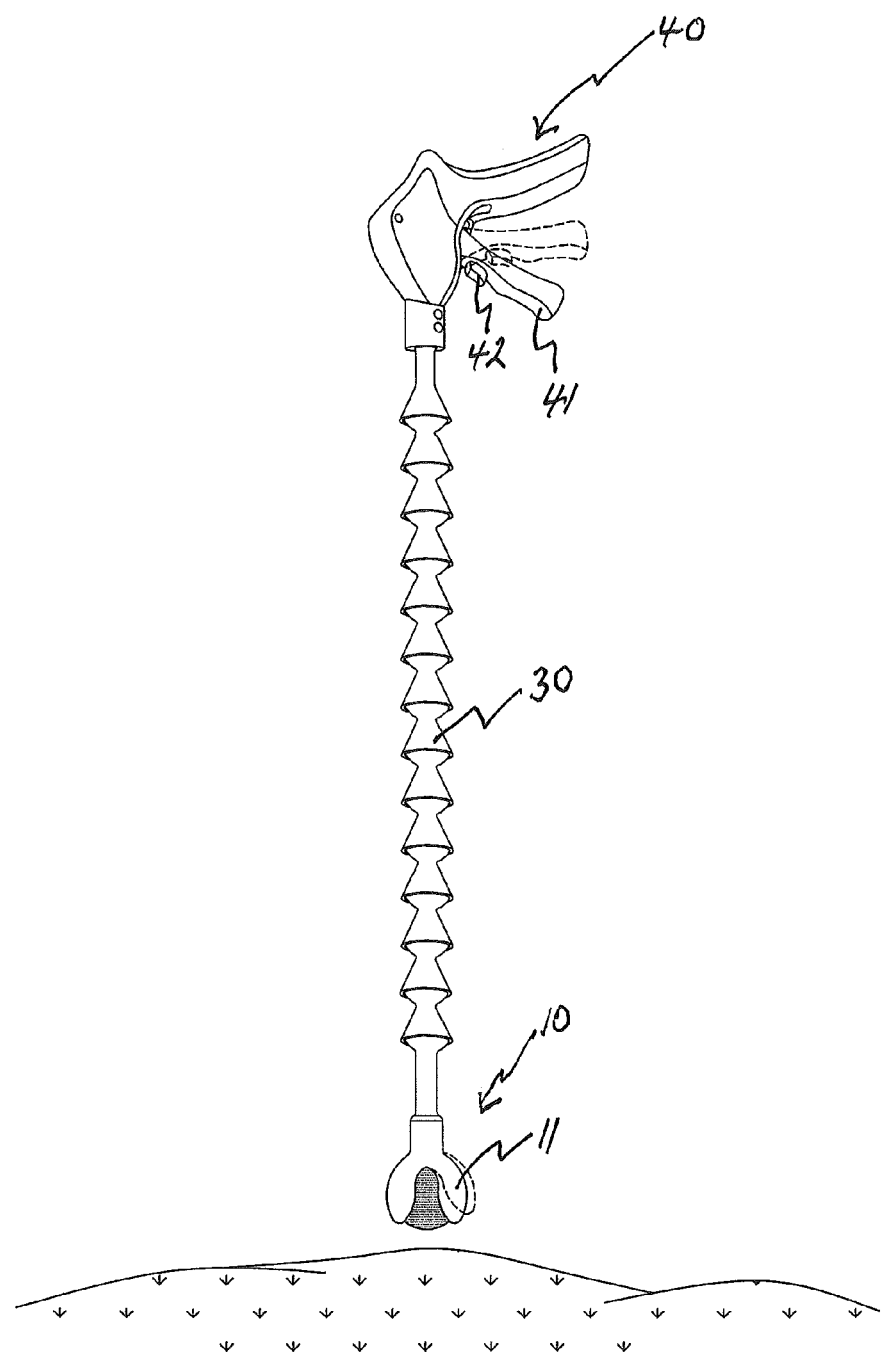
FIG. 16 shows an embodiment of the present invention where the jaw/claw end portion is shaped and sized to reversibly retain a golf ball, with at least one jaw/claw member being movable via operation of the trigger on the remote handle.
Figure 17:
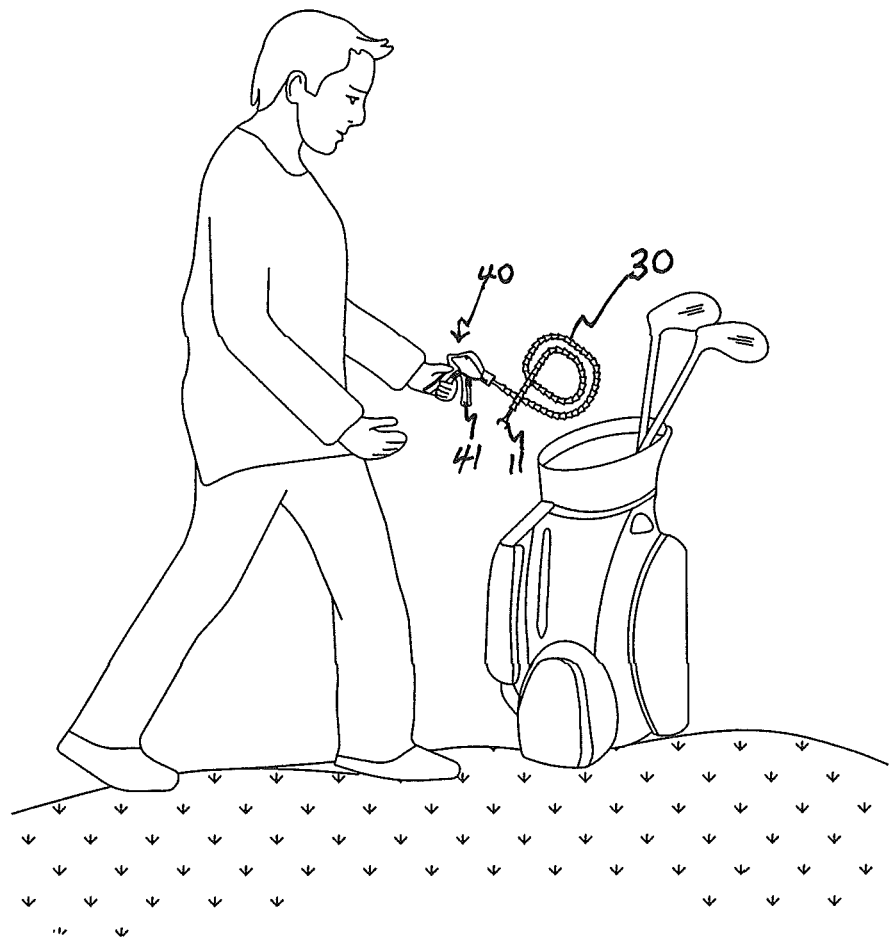
FIG. 17 illustrates a golfer with a coiled configuration of the device pictured in FIG. 13.

According to certain embodiments of the present invention, a hand operated device for grasping a golf ball from the ground from a standing position is provided where the device includes a flexible, preferably corrugated extendable member 30 having a triggered handle 40 at one end and at the other, a jaw/claw assembly 10 such that a golf ball can be grasped and manipulated. FIGS. 13-17 are generally directed to various embodiments directed to golf-related aspects of the present invention. FIG. 13 shows an embodiment where the claw portion 10 is adapted to encircle a golf ball and golf tee, with the flexible central portion 30 able to be extended into a linear configuration to enable a golfer to plant the ball/tee into the ground. FIG. 14 shows an embodiment where the flexible central portion 30 assumes a linear configuration to facilitate teeing of a ball, with a stabilizing pogo-stick type member 60 associated with the lower portion of the device. FIG. 15 shows an embodiment of the present invention where a separate articulated member 61 provides stability for the teeing operation, with the shorter articulated arm 61 designed to bend when contacted with the ground as the tee is forced downwardly by a golfer pressing down on the handle. FIG. 16 shows an embodiment where the jaw/claw end portion 10 is shaped and sized to reversibly retain a golf ball, with at least one jaw/claw member 11 being movable via operation of the trigger 41 on the remote handle 40. And FIG. 17 illustrates a golfer with a coiled configuration of the device pictured in FIG. 13. One will appreciate, however, that due to the flexible nature of the device, it is possible to construct versions that have very long extended portions but that can be coiled compactly so that a golfer is able to easily retrieve balls hit into the water or rough. For example, in certain embodiments, while the flexible line 30 is provided such that it is not rigid enough to hold a golf ball in an extended position without bending, the flexible extension 30 can be 6 feet, more preferably 10 feet, and in some embodiments 15 to 25 feet or more—such that one is able to stand on the shore of a golf pond/lake and retrieve submerged golf balls that are deep or remote from shore. The flexible nature of the device permits one to reach balls that may be in-between rocks, stuck in the mud or otherwise positioned in a way that a straight, rigid golf ball retrieving device simply could not accommodate. In other embodiments, the length of the flexible device 30 can be varied as desired by detaching or attaching additional lengths of the preferred articulated, ball-and-socket portions or segments until a desired length is archived. Thus, while in some embodiments, the ball- and socket connections are very difficult to separate—especially without a special tool (such as one available for loc-line, Lockwood Products), in other embodiments, the ability to reversibly attach members or segments is facilitated by a less secure connection, while still retaining the desired ability to manipulate the device once assembled. The cord extending through the hollow interior of the flexible portion is also adjustable (such as it is in telescoping arrangements otherwise described herein).

As discussed herein in further preferred embodiments, a stabilizer 60, 61 for stabilizing the device during teeing of a golf ball is provided, with such stabilizer preferably made from similar material as the main extendable member: e.g. loc-line elements connected together that are flexible. Thus, when such flexible stabilizer 61 is secured adjacent to and substantially parallel with the main extended member of the device, such as about 8 inches or so form the jaw/claw end 10 of the device, it is able to extend to reach the ground to achieve desired stability during the teeing operation. The short arm 61 is readily and easily bent out of the way when the golfer does not need such stabilizer function. Manipulating of a golf ball may comprise picking the ball up from the ground; and/or placing the ball on the ground; and/or inserting the golf tee with ball associated therewith object at least partly into the ground. In preferred embodiments, the manipulator includes a gripper 10 with opposed pivoting jaws 11.

Moreover, in addition to assisting golfers in teeing off without having to bend down to the ground, the present invention is very useful in retrieving balls that land in difficult to reach places on a golf course, such as out of bounds, in shallow water of golf lakes or ponds, in bushes, tangled trees, etc. It can further be used to place a marker and retrieve a ball once in the hole. Thus in one embodiment, a golfer takes a ball and a tee, loads them into the closable jaws/claws of the device, compresses the trigger of the device to hold the jaws around the ball and tee combination, points the tee towards the ground and inserts the tee into the ground. Using the present device, a golfer can readily unwind the coiled device, stretch it and bend it as desired to reach any ball in the rough, undergrowth, off the fairway or in the water, with relative ease and without having to otherwise bend down. After use, it can be coiled again and stowed with a golf bag or on the cart. Incorporated herein by this reference are the following references to further assist in complying with written description and enablement requirements: U.S. Pat. No. 6,971,695 to Backstrom; U.S. Pat. No. 5,707,303 to Berkowitz, et. al., U.S. Pat. No. 8,529,379 to Faircloth; and U.S. Pat. No. 8,602,917 to Bennett.

In one embodiment, a stabilizer feature 60 is employed with the flexible jaw/claw device 10 described herein for the purpose of assisting in stabilizing the placement of a golf ball on a tee into the ground for a golfer to tee off. Thus, in one embodiment, the stabilizer 60 comprises a ground engaging foot and a resilient member to urge the foot to an extended position. The stabilizer 60 may be connected to the lower portion of the extended member so that when lowered to the ground, contact the ground to stabilize the ball placement operation are arranged such that the foot engages with the ground, and as the manipulator is moved towards the ground against the urging of the resilient member, the foot remains engaged with the ground to stabilize the device while the control mechanism is operated to manipulate the object. In a preferred embodiment, the cost and expense and complexity of a spring loaded pogo-stick-like element 60 is avoided in favor of a length of loc-line hose 61 that is associated with the main loc-line member connecting the handle and the jaws/claws 11. Thus, about 6-10 inches of preferably ¼ inch diameter loc-line (although ½ inch loc-line may also be used) is connected to the main loc-line member (preferably comprised of inch loc-line due to its more stable characteristics—and ability to convey the downward forces from the handle to the ground exerted by a golfers pressing in his/her tee) to act as a short, stabilizing, ground contacting extension. When a golfer presses down on the tee with the device, the ¼ inch loc-line bends due to the contact with the ground, thus providing just enough resistive force to stabilize the tee placing operation without hindering the same. Also incorporated herein by this reference is U.S. Pat. Publication No. 20130130842 (application Ser. No. 13/673,032) to Bennett. Thus, in other embodiments the stabilizer 60 comprises a piston arranged to move axially within a tube which, in use, is secured to the flexible shaft member 30 of the device, extending substantially parallel with the shaft. A ground engaging foot and a resilient member is provided to urge the foot towards an extended position.

While in a preferred embodiment, the jaws/claw 10 is designed and adapted for holding a golf ball and a tee, in others, it may just hold a golf ball alone—and in still others, just a tee alone. Preferably, however, the jaws/claws 11 accommodate insertion of the tee with the golf ball resting on it. In various embodiments, the distal end portions can be substituted with differently configured mechanisms, such as the replacement of a gripper jaw end with a pooper-scooper end or a golf ball gripping device. Thus, in certain embodiments, with one device having the handle 40, trigger 41 and flexible central portion 30, one can achieve a myriad of different desired operations simply by removing and replacing end tools that have complementary detachable housings associated therewith that interact and reversibly connect to the non-handle end of the tool.

For example, an departing from a strictly movable jaw member embodiment, certain embodiments of the present invention are directed to a golf ball cupping member (as depicted in FIG. 16) but that may have flexible, rubber-like memory features to reversibly encompass a golf ball (rather than moving jaw features) and be either integrally connected or reversibly connected to the distal end of a column portion having the flexible, corrugated construction as described herein. In such an embodiment, there is no necessity of having a active handle with a trigger mechanism, as the ability to reversibly pick up a golf ball via the ball cupping structure of the resilient rubber/plastic cup is sufficient to achieve such a ball recovery operation. The tool having the cup at its end can be coiled and carried readily by a golfer to assist in picking up balls in various environments, including but not limited to after hitting the ball into the cup, to retrieve balls in the rough, etc. In one embodiment, a magnetic ball placement marker is provided in the upper-most portion of the distal golf ball receiving end of a device, with a strong magnet associated therewith to pick up a metal or magnetic golf ball marker form the ground. In particular embodiments, the handle/trigger assembly as described herein is employed to move a magnet into and out of vertical position next to the distal end of the ball cup. In such a manner, a golfer is able to insert a metal or magnetic ball marker into such distal end (which has a strong magnet associated therewith and that is operably connected to a cord that extends to the handle and is operated flexibly adjust the tool so that the distal end is positioned near the ground. The trigger is then operated to move the magnet vertically and out of the area of the end of the ball cup, thus causing the magnetic attraction to grow weak and the ball marker to be free to descend to the ground. When picking up the marker, the magnet attached to the cord is permitted or moved to the distal and of the tool, thus permitting the ball marker to be magnetically attracted and retrieved by the tool the golfer can then flex and bend the tool so as to retrieve the ball marker (as he can further retrieve the ball.)

While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention. It is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

What is claimed is:

1. A pet waste collection device, comprising a retracting animal leash device, said animal leash device including a housing having a handle portion adapted to be grasped in the hand of a user and a reservoir portion adapted to store an elongate leash; a spool rotatably mounted within said reservoir portion; and an elongate leash positioned about said spool and extendable from said reservoir portion;

a pair of jaws movable between a fully clamped position and a fully opened position;

said handle portion spaced apart from the pair of jaws by a central portion, the central portion comprising at least two separate portions comprising a hollow, corrugated member having alternating ridges and grooves, said corrugated member being bendable so as to attain a predetermined shape so that a user can preposition said central portion into a desired bent configuration;

wherein the handle portion comprises a first manually-actuatable trigger operatively connected to the pair of jaws by a pull member at least substantially disposed within the central portion, whereby actuation of the trigger is operative to move the pull member to thereby selectively position the pair of jaws between the fully clamped position and the fully opened position;

wherein said pull member comprises at least one cord operatively connecting the handle portion to the pair of jaws, said at least one cord extending through said central portion.

2. The device as set forth in claim 1, wherein the at least two separate portions of the central portion comprise a plurality of interconnected connectors which together define a passageway through which said pull member passes through.

3. The device as set forth in claim 1, wherein said at least two separate portions comprise a plurality of connector bodies that interconnect with each other.

4. The device as set forth in claim 1, wherein at least ⅔rds of the central portion comprises said corrugated member.

5. The device as set forth in claim 1, wherein the central portion comprises a corrugated member that is adapted to be coiled to facilitate transportation and storage.

6. The device as set forth in claim 1, wherein the central portion comprises a corrugated member made of two or more corrugated members provided at different relative locations along the central portion of the device.

7. The device as set forth in claim 1, wherein said corrugated member comprises a plurality of interconnected connectors in engagement with each other.

8. The device as set forth in claim 1, wherein said jaws are adapted to receive a bag removeably secured in place over said jaws when said jaws are in said fully opened position.

9. The device as set forth in claim 1, wherein said jaws are shaped as claw halves and when the trigger is operated, close together to permit encompassing waste in between said claw halves.

10. A pet waste collection device comprising:

a jaw portion comprising a pair of jaws having a scooped shape adapted to encompass pet waste and movable relative to each other between fully clamped and fully opened positions thereof; a handle portion spaced apart from the jaw portion by a selectively extendible central portion, the handle portion comprising a first manually-actuatable trigger operatively connected to the jaw portion by at least one cord that is at least substantially disposed within the central portion, whereby actuation of the trigger is operative to move the at least one cord to thereby selectively position the pair of jaws between the fully clamped and fully opened position thereof; said central portion being at least three inches in length comprising a hollow, corrugated member having alternating ridges and grooves, said member being bendable so as to attain a predetermined shape; the at least one cord operatively connecting the handle portion to the jaw portion and extending through said central portion;

wherein the corrugated member is connected to a retracting animal leash device, that includes a housing, wherein said handle portion is associated with said housing, and wherein said handle portion is adapted to be grasped in the hand of a user, said animal leash device having a reservoir portion adapted to store an elongate leash; a spool rotatably mounted within said reservoir portion; and an elongate leash positioned about said spool and extendable from said reservoir portion.

11. The device of claim 10, wherein at least ⅔rds of said central portion comprises said corrugated member.

12. The device of claim 10, wherein at least a portion of said central portion is in telescoping relationship with an adjacent portion of said central portion.

13. The device of claim 10, further comprising a locking member associated with said central portion to fix two adjacent members of said central portion in an engaged position, said locking member operable between a first locking position and a second unlocking position.

14. The device as set forth in claim 10, wherein said jaws are adapted to receive a bag removeably secured in place over said jaws when said jaws are in said fully opened position.

15. The device of claim 10, wherein the manually-actuatable trigger causing the reversible opening and closing of the jaws.

16. The device as set forth in claim 10, wherein said corrugated member comprises a plurality of interconnected connectors in engagement with each other.

17. The device as set forth in claim 10, wherein said corrugated member comprises a plurality of connector bodies that interconnect with each other.

18. A pet waste collection device comprising, a jaw portion comprising a pair of jaws movable relative to each other between fully clamped and fully opened positions thereof; a handle portion spaced apart from the jaw portion by a selectively extendible central portion, the handle portion comprising a first manually-actuatable trigger operatively connected to the jaw portion by a selectively extendible pull member at least substantially disposed within the central portion, whereby actuation of the trigger is operative to move the pull member to thereby selectively position the pair of jaws between the fully clamped and fully opened position thereof, whereby said fully clamped position is achieved when said trigger is pulled; wherein said central portion comprises a hollow, corrugated member having alternating ridges and grooves, said corrugated member constructed of plastic and being bendable so as to attain a predetermined shape; said pull member comprising at least one cord operatively connecting the handle portion to the jaw portion, said at least one cord extending through said corrugated member and being entirely encompassed by said central portion;

wherein the corrugated member is connected to a retracting animal leash device that includes a housing, wherein said handle portion is associated with said housing, and wherein said handle portion is adapted to be grasped in the hand of a user, said animal leash device having a reservoir portion adapted to store an elongate leash; a spool rotatably mounted within said reservoir portion; and an elongate leash positioned about said spool and extendable from said reservoir portion.

19. The device of claim 18, further comprising a locking member associated with said central portion to fix two adjacent members of said central portion in an engaged position, said locking member operable between a first locking position and a second unlocking position.

20. The device as set forth in claim 18, wherein said jaws are adapted to receive a bag removeably secured in place over said jaws when said jaws are in said fully opened position.

\* \* \* \* \*